(12) United States Patent
Motai

(10) Patent No.: US 9,693,815 B2
(45) Date of Patent: Jul. 4, 2017

(54) SURGICAL INSTRUMENT

(71) Applicant: OLYMPUS CORPORATION, Tokyo (JP)

(72) Inventor: Kosuke Motai, Hidaka (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/399,128

(22) Filed: Jan. 5, 2017

(65) Prior Publication Data

US 2017/0112561 A1   Apr. 27, 2017

Related U.S. Application Data

(63) Continuation of application No. PCT/JP2015/075701, filed on Sep. 10, 2015.

(30) Foreign Application Priority Data

Oct. 31, 2014   (JP) .................................. 2014-222759

(51) Int. Cl.
| | | |
|---|---|---|
| *A61B 17/072* | (2006.01) | |
| *A61B 18/08* | (2006.01) | |
| *A61B 17/28* | (2006.01) | |
| *A61B 17/04* | (2006.01) | |

(52) U.S. Cl.
CPC ........ *A61B 18/085* (2013.01); *A61B 17/0469* (2013.01); *A61B 17/07207* (2013.01); *A61B 17/28* (2013.01); *A61B 18/08* (2013.01); *A61B 2017/07285* (2013.01)

(58) Field of Classification Search
CPC ... A61B 18/08; A61B 18/085; A61B 17/0469; A61B 17/07207; A61B 17/28; A61B 2017/08285
See application file for complete search history.

(56) References Cited

U.S. PATENT DOCUMENTS

| | | | | |
|---|---|---|---|---|
| 5,665,100 | A   * | 9/1997 | Yoon ................ | A61B 17/12013 606/139 |
| 8,640,940 | B2 * | 2/2014 | Ohdaira ........... | A61B 17/07207 227/175.1 |
| 2009/0270852 | A1* | 10/2009 | Takashino ............ | A61B 18/085 606/27 |

(Continued)

FOREIGN PATENT DOCUMENTS

| | | |
|---|---|---|
| JP | H10-508781 A | 9/1998 |
| JP | 2002-085414 A | 3/2002 |

(Continued)

OTHER PUBLICATIONS

International Search Report dated Dec. 1, 2015 issued in PCT/JP2015/075701.

*Primary Examiner* — Andrew M Tecco
(74) *Attorney, Agent, or Firm* — Scully, Scott, Murphy & Presser, PC

(57) ABSTRACT

A surgical instrument includes a first jaw and a second jaw serving as grasping parts, a first joining part, a first dissecting part, a second joining part, a second dissecting part, and a tissue preservation part disposed between the first joining part and the second joining part and configured to preserve a non-joining region between the first joining part and the second joining part when the first joining part and the second joining part join living body tissue.

7 Claims, 29 Drawing Sheets

(56) References Cited

U.S. PATENT DOCUMENTS

| | | | | |
|---|---|---|---|---|
| 2011/0095067 A1* | 4/2011 | Ohdaira | ............... | A61B 17/115 |
| | | | | 227/175.2 |
| 2012/0071871 A1* | 3/2012 | Lue | ................... | A61B 18/1445 |
| | | | | 606/33 |
| 2012/0080344 A1* | 4/2012 | Shelton, IV | ........... | A61B 90/92 |
| | | | | 206/438 |

FOREIGN PATENT DOCUMENTS

| | | |
|---|---|---|
| JP | 2009-261907 A | 11/2009 |
| JP | 2010-508068 A | 3/2010 |
| WO | WO 96/22056 A1 | 7/1996 |
| WO | WO 2008/057281 A2 | 5/2008 |
| WO | WO 2009/133875 A1 | 11/2009 |

\* cited by examiner

SURGICAL INSTRUMENT

This application is a continuation application, based on PCT/JP2015/075701, filed on Sep. 10, 2015, claiming priority based on Japanese Patent Application No. 2014-222759, filed on Oct. 31, 2014, the content of which is incorporated herein by reference.

FIELD OF THE INVENTION

The present invention relates to a surgical instrument.

DESCRIPTION OF THE RELATED ART

In the related art, various instruments configured to perform treatment on living body tissue are known (for example, see Published Japanese Translation No. H10-508781 of the PCT International Publication and Japanese Unexamined Patent Application, First Publication No. 2002-85414). Various improvements of medical instruments according to requirements of users or the like are performed to improve workability with respect to a treatment target.

For example, as disclosed in Published Japanese Translation No. 2010-508068 of the PCT International Publication, a surgical instrument capable of accomplishing grasping, separation and suture of tissue using a series of operations is known.

SUMMARY OF THE INVENTION

Means for Solving the Problem

An aspect of the present invention is a surgical instrument including: a pair of grasping parts having distal end portions and proximal end portions, having shapes extending along a longitudinal central axis connecting the distal end portions and the proximal end portions, and having a pair of grasping surfaces disposed to face each other such that the pair of grasping surfaces are capable of grasping living body tissue; a first joining part disposed at the vicinity of the distal end portion of the grasping part and configured to irreversibly join the living body tissue grasped by the pair of grasping parts; a first dissecting part configured to cut the living body tissue joined by the first joining part in a region in which the living body tissue is joined by the first joining part in a longitudinal central axis direction; a second joining part disposed away from the first joining part, disposed at the vicinity of the proximal end portion of the grasping part, and configured to irreversibly join the living body tissue grasped by the pair of grasping parts; a second dissecting part configured to cut the living body tissue joined by the second joining part in a region in which the living body tissue is joined by the second joining part in the longitudinal central axis direction; and a tissue preservation part disposed between the first joining part and the second joining part, having a recessed portion formed to be recessed with respect to the pair of grasping surface and disposed at the pair of grasping surfaces such that the tissue preservation part is configured to preserve a non-joining region between the first joining part and the second joining part when the first joining part and the second joining part join the living body tissue.

At least one of the first joining part and the second joining part may have a thermal bonding mechanism configured to apply thermal energy by electricity to the living body tissue and adhesively join a plurality of tissues in a state in which the plurality of tissues separated from each other are grasped by the pair of grasping parts.

At least one of the first joining part and the second joining part may have a stapling mechanism configured to couple staples to the living body tissue and adhesively connect a plurality of tissues using the staples in a state in which the plurality of tissues separated from each other are grasped by the pair of grasping parts.

The first dissecting part may have a first tissue separating structure set to a position at which a joinable region by the first joining part is interposed between the recessed portion and the first dissecting part and elongated in the longitudinal central axis direction, and the second dissecting part may have a second tissue separating structure set to a position at which a joinable region by the first joining part is interposed between the recessed portion and the second dissecting part and elongated in the longitudinal central axis direction.

A length of the first dissecting part measured along the longitudinal central axis direction may be larger than that of the second dissecting part measured along the longitudinal central axis direction.

The surgical instrument may further include an opening/closing operation part configured to open and close the pair of grasping parts; a joining operation part configured to join the living body tissue using at least one of the first joining part and the second joining part by individually moving the first joining part and the second joining part; and a separating operation part configured to cut the living body tissue using at least one of the first dissecting part and the second dissecting part by individually moving the first dissecting part and the second dissecting part according to operation that is different from operation of the joining operation part.

The surgical instrument may further include an opening/closing operation part configured to open and close the pair of grasping parts; and a suture/separating simultaneous operation section configured to move the first joining part, the second joining part, the first dissecting part and the second dissecting part through a single operation.

DETAILED DESCRIPTION OF THE INVENTION

First Embodiment

A first embodiment of the present invention will be described.

Figure 1:
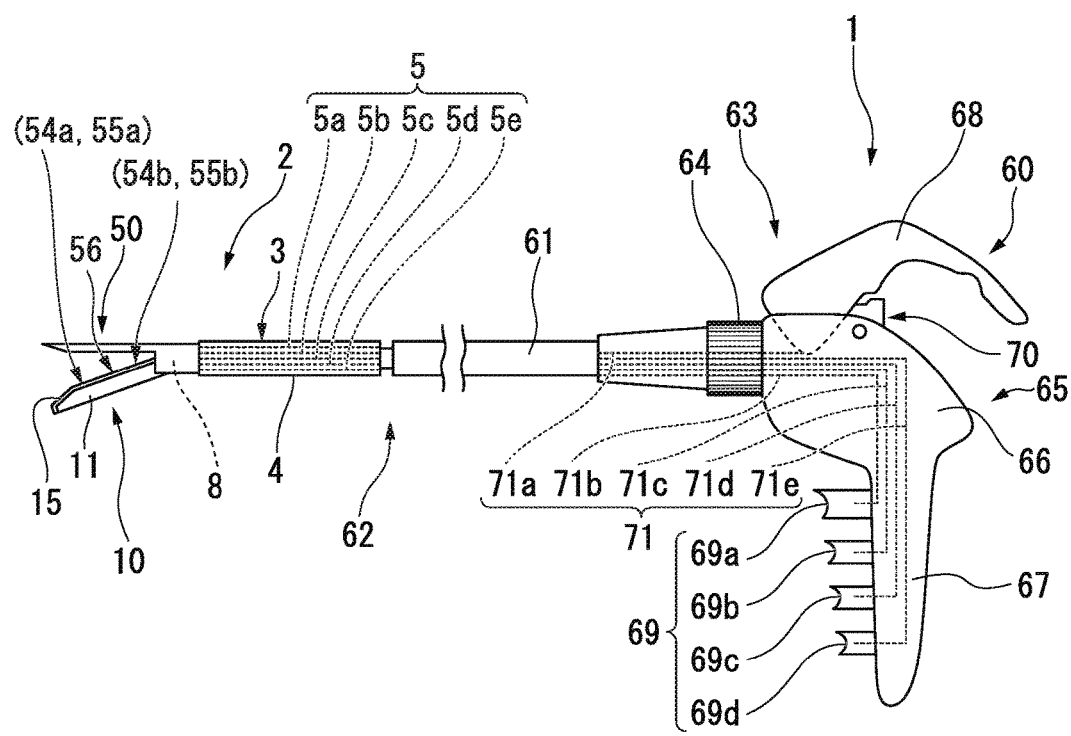
FIG. 1 is a side view of a surgical instrument of a first embodiment of the present invention.
Figure 2:
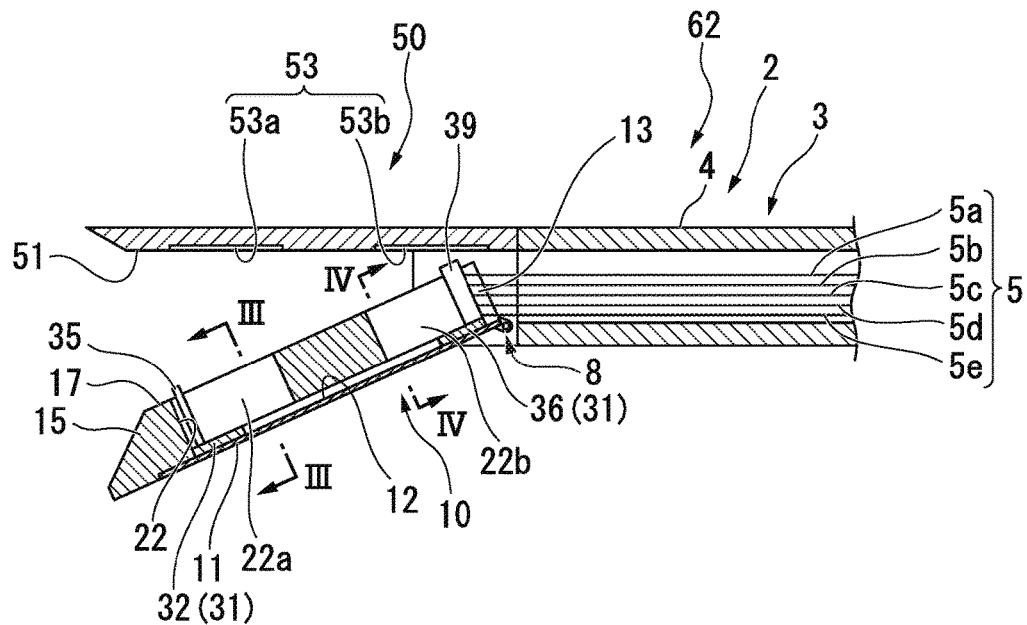
FIG. 2 is a cross-sectional view of a cartridge of the surgical instrument.
Figure 3:
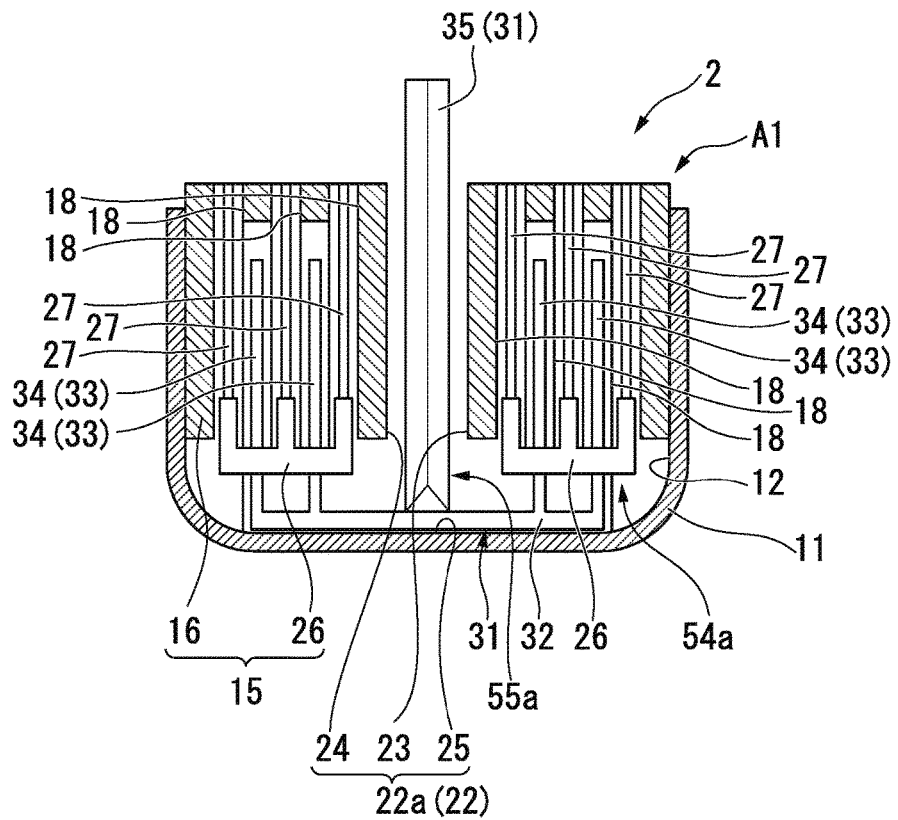
FIG. 3 is a cross-sectional view taken along line III-III of FIG. 2.
Figure 4:
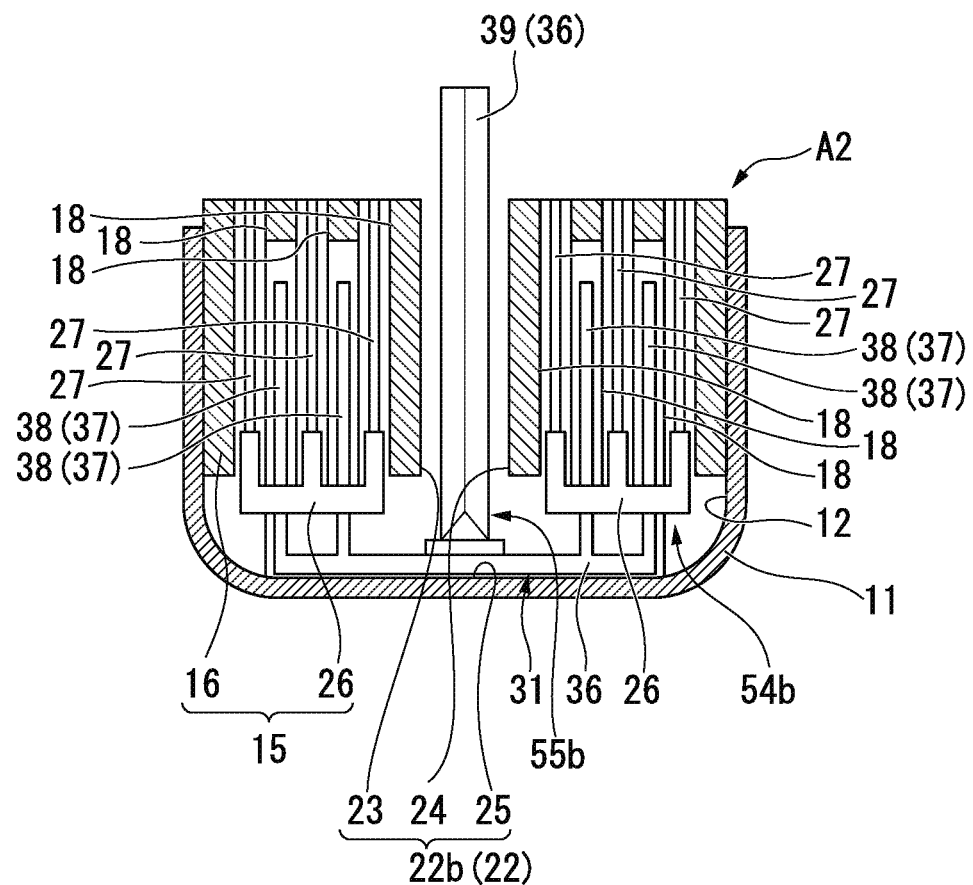
FIG. 4 is a cross-sectional view taken along line IV-IV of FIG. 2.

FIG. 1 is a side view of a surgical instrument of the embodiment. FIG. 2 is a cross-sectional view of a cartridge of the surgical instrument of the embodiment. FIG. 3 is a cross-sectional view taken along line III-III of FIG. 2. FIG. 4 is a cross-sectional view taken along line IV-IV of FIG. 2.

Figure 5:
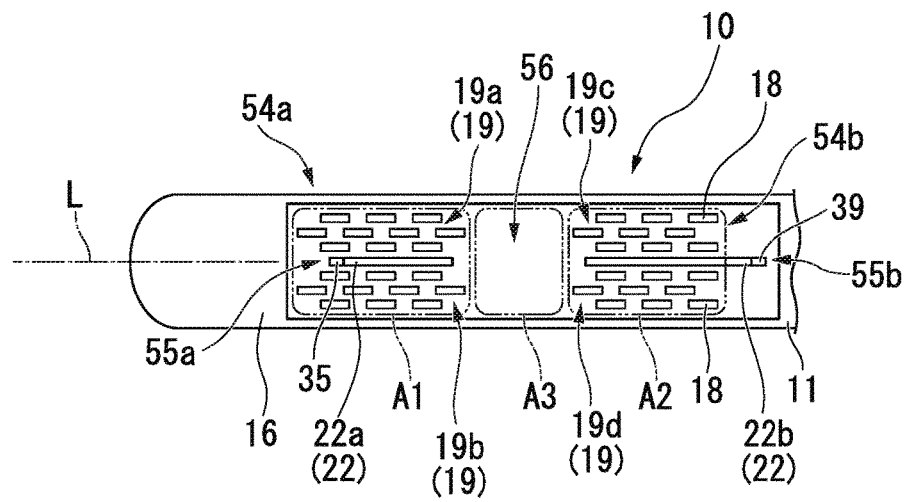
FIG. 5 is a plan view of a first jaw of the cartridge.
Figure 6:
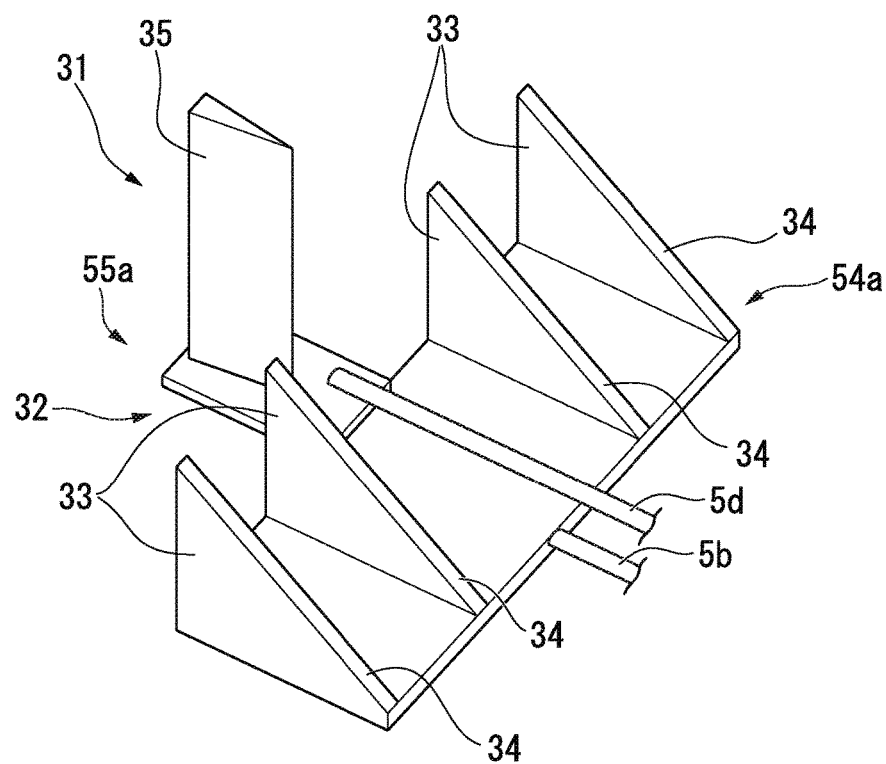
FIG. 6 is a perspective view of a first actuation part disposed in the first jaw.
Figure 7:
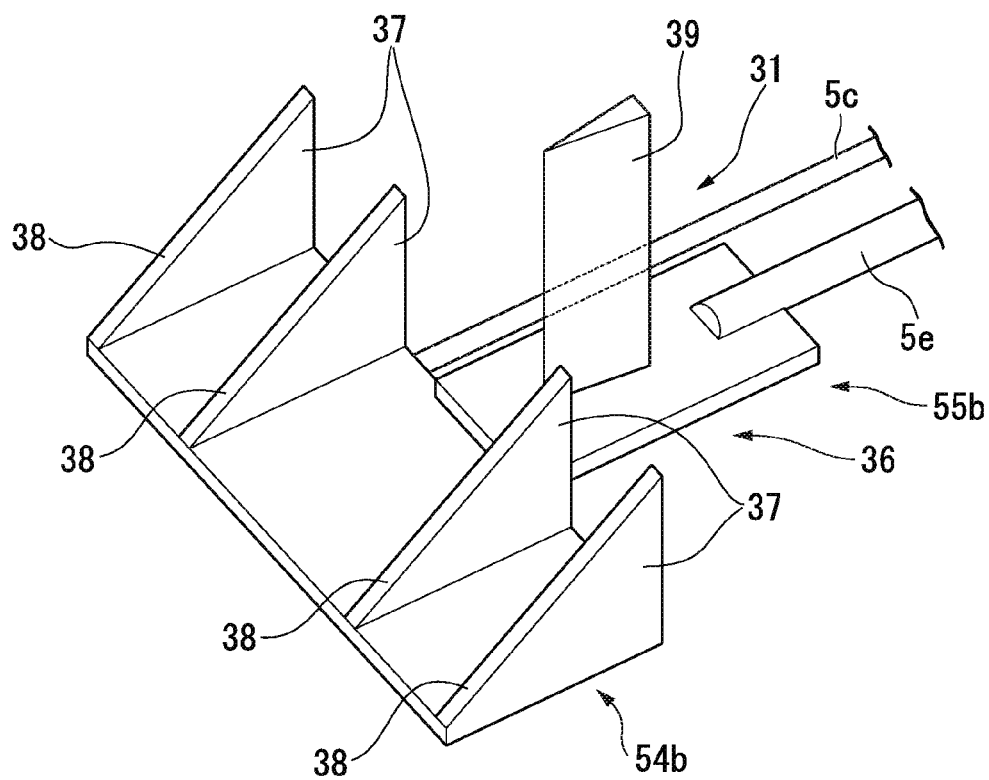
FIG. 7 is a perspective view of a second actuation part disposed in a second jaw.
Figure 8:
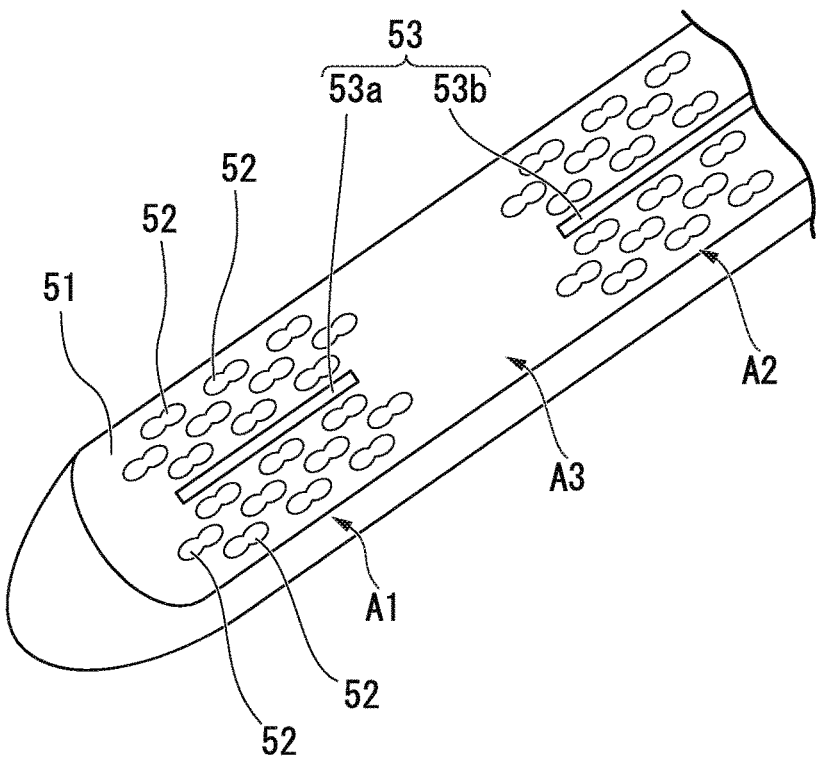
FIG. 8 is a rear view of the second jaw of the cartridge.
Figure 9:
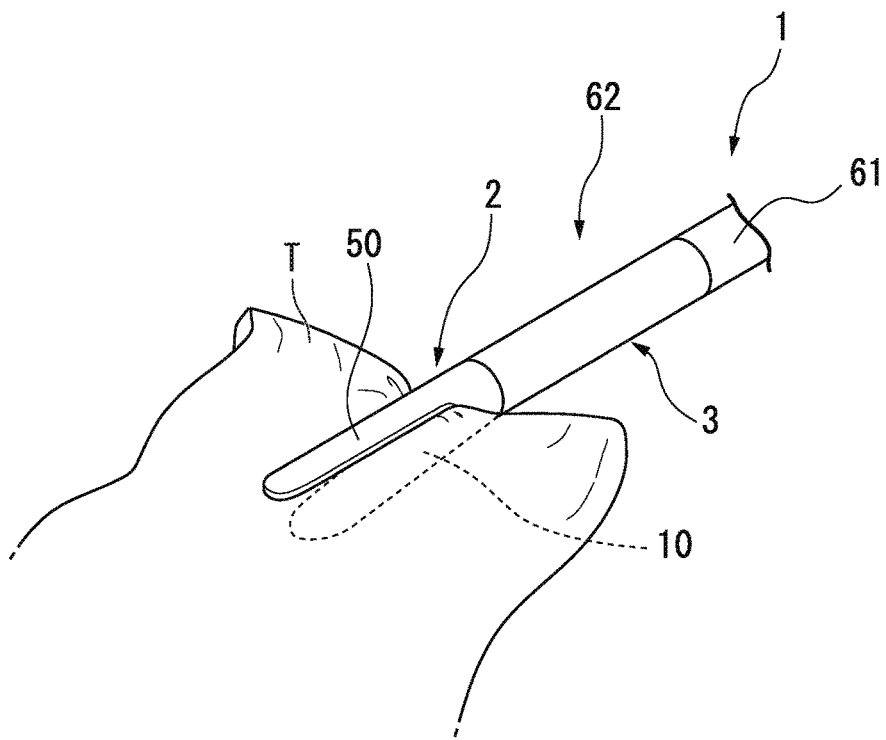
FIG. 9 is a perspective view showing a state in which living body tissue is grasped using the surgical instrument.
Figure 10:
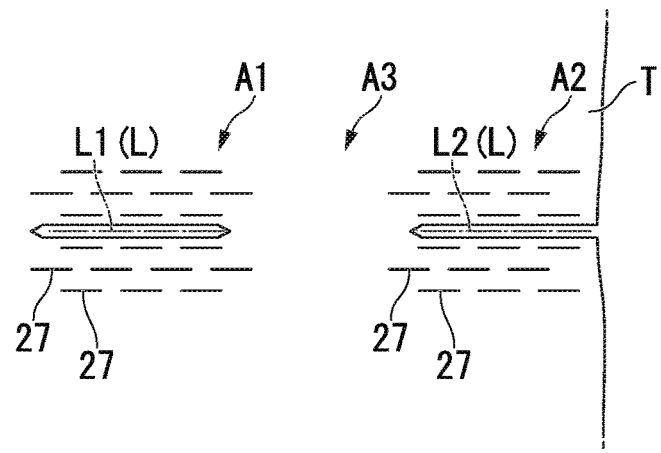
FIG. 10 is a schematic view showing an example of joining and separating of living body tissue using the surgical instrument.
Figure 11:
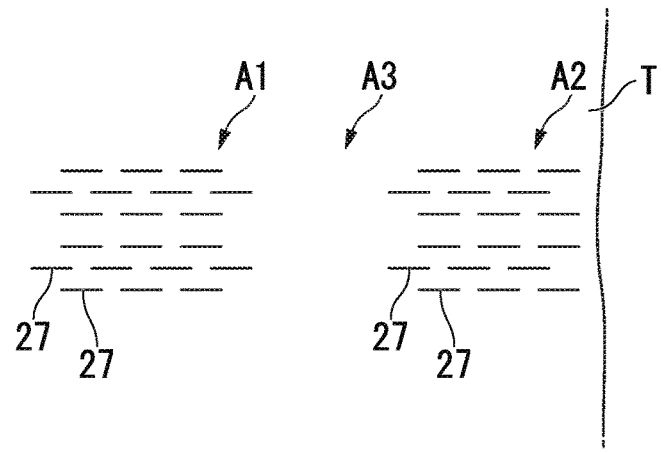
FIG. 11 is a schematic view showing another example of joining and separating of living body tissue using the surgical instrument.
Figure 12:
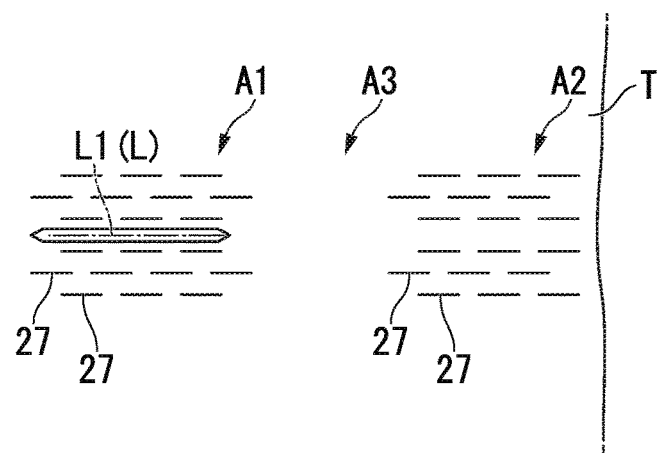
FIG. 12 is a schematic view showing still another example of joining and separating of living body tissue using the surgical instrument.

FIG. 5 is a plan view of a first jaw of the cartridge of the surgical instrument of the embodiment. FIG. 6 is a perspective view of a first actuation part disposed in the first jaw. FIG. 7 is a perspective view of a second actuation part disposed in a second jaw. FIG. 8 is a rear view of the second jaw of the cartridge of the surgical instrument of the embodiment. FIG. 9 is a perspective view showing a state in which living body tissue is grasped using the surgical instrument of the embodiment. FIG. 10 is a schematic view showing an example of joining and separating of living body tissue using the surgical instrument of the embodiment. FIG. 11 is a schematic view showing another example of joining and separating of living body tissue using the surgical instrument of the embodiment. FIG. 12 is a schematic view showing still another example of joining and separating of living body tissue using the surgical instrument of the embodiment.

A surgical instrument 1 of the embodiment shown in FIG. 1 is a medical instrument (for example, see FIG. 10) configured to staple living body tissue T1 using staples 27 and separate the sutured area.

As shown in FIG. 1, the surgical instrument 1 has a cartridge 2 in which the staples 27 (see FIG. 3) are loaded, and a stapler 60 to which the cartridge 2 is capable of being attached.

As shown in FIGS. 2 and 3, the cartridge 2 has a shaft section 3, an opening/closing link section 8, and a first jaw 10 and a second jaw 50 that constitute a pair of grasping parts.

The shaft section 3 is a substantially rod-shaped area that is able to connect the cartridge 2 to the stapler 60.

The shaft section 3 has a tubular section 4 and connecting members 5.

The connecting members 5 are disposed in the tubular section 4. A proximal end of the tubular section 4 can be connected to a distal end of a shaft 61 (to be described below) of the stapler 60. A distal end of the tubular section 4 is connected to the opening/closing link section 8 and the second jaw 50.

The connecting members 5 (a first connecting member 5a, a second connecting member 5b, a third connecting member 5c, a fourth connecting member 5d and a fifth connecting member 5e) are members operated by operation by a user on the stapler 60.

The first connecting member 5a is a substantially rod-shaped member configured to open and close the first jaw 10 with respect to the second jaw 50. A proximal end of the first connecting member 5a is capable of being connected to a distal end of a first transmission member 71a of a transmission member 71 (see FIG. 1, which will be described below). A distal end of the first connecting member 5a is connected to the opening/closing link section 8.

The second connecting member 5b is a substantially rod-shaped member configured to operate a first joining part 54a (to be described below). A proximal end of the second connecting member 5b is capable of being connected to a distal end of a second transmission member 71b of the transmission member 71 (to be described below). As shown in FIG. 6, the distal end of the second connecting member 5b is connected to a first cam 33 which is a portion of the first joining part 54a. Further, in the embodiment, since the second connecting member 5b is a member configured to operate a first joining part by mainly pulling the member, for example, the member may be a flexible member such as a wire or the like.

The third connecting member 5c is a substantially rod-shaped member configured to operate a second joining part 54b (to be described below). A proximal end of the third connecting member 5c is capable of being connected to a distal end of a third transmission member 71c of the transmission member 71 (to be described below). As shown in FIG. 7, the distal end of the third connecting member 5c is connected to a second cam 37 which is a portion of the second joining part 54b.

The fourth connecting member 5d is a substantially rod-shaped member configured to operate a first dissecting part 55a (to be described below). A proximal end of the fourth connecting member 5d is capable of being connected to a distal end of a fourth transmission member 71d of the transmission member 71 (to be described below). As shown in FIG. 6, a distal end of the fourth connecting member 5d is connected to a first dissecting knife 35 which is a portion of the first dissecting part 55a. Further, in the embodiment, since the fourth connecting member 5d is a member configured to operate the first dissecting part by mainly pulling the member, for example, the member may be a flexible member such as a wire or the like.

The fifth connecting member 5e is a substantially rod-shaped member configured to operate a second dissecting part 55b (to be described below). A proximal end of the fifth connecting member 5e is capable of being connected to a distal end of a fifth transmission member 71e of the transmission member 71 (to be described below). As shown in FIG. 7, a distal end of the fifth connecting member 5e is connected to a second dissecting knife 39 which is a portion of the second dissecting part 55b.

The opening/closing link section 8 shown in FIG. 2 has a link structure configured to convert movement of the first connecting member 5a in the central axis direction of the first connecting member 5a into opening/closing movement of the first jaw 10.

As shown in FIGS. 2, 3 and 4, the first jaw 10 has a base section 11, a staple holder 15, the staples 27 and an actuation part 31.

The base section 11 is a substantially rod-shaped or channel-shaped member having a longitudinal axis.

The base section 11 has a concave portion 12 which is capable of housing the staple holder 15 and the actuation part 31, and a communication path 13 with the shaft section 3.

The concave portion 12 is opened toward a second grasping surface 51 of the second jaw 50.

The communication path 13 with the shaft section 3 is a passage through which the connecting member 5 is inserted.

The staple holder 15 has a holder body portion 16 and a driver 26.

The holder body portion 16 has a first grasping surface 17 configured to come in contact with tissue when the tissue is grasped, an housing portion 18 in which the staples 27 are housed, and a groove portion 22 opened at the first grasping surface 17. The holder body portion 16 is attached to the concave portion 12 of the base section 11 in a direction in which the first grasping surface 17 is exposed from the base section 11.

The first grasping surface 17 is a surface directed toward the second grasping surface 51 of the second jaw 50 in a state in which the holder body portion 16 is attached to the concave portion 12 of the base section 11.

The housing portion 18 shown in FIGS. 3, 4 and 5 can house the staples 27 in a state in which insertion ends of the staples 27 are directed toward the second grasping surface 51.

As shown in FIG. 5, in the first grasping surface 17, an inner region of an envelope curve that surrounds the plurality of accommodating portions 18 defines a first suture region (a first joining region) A1 and a second suture region (a second joining region) A2 in which the tissue is sutured by the staples 27. The first suture region A1 is a region disposed in the vicinity of a distal end portion of the first jaw 10. The second suture region A2 is a region disposed in the vicinity of a proximal end of the first jaw 10. The first suture region A1 and the second suture region A2 are separated with a preservation region A3 therebetween. Further, the preservation region A3 is a region in which the staples 27 and the housing portion 18 thereof are not installed and suture of living body tissue is not performed.

In a state in which the staples 27 are housed in the housing portion 18, staple arrays 19 (a distal end first staple array 19a, a distal end second staple array 19b, a proximal end first staple array 19c, a proximal end second staple array 19d) are constituted in four regions divided by the groove portion 22 and also divided by the preservation region A3.

The distal end first staple array 19a and the proximal end first staple array 19c are constituted by the plurality of staples 27 arranged in a direction in which the groove portion 22 extends. In the embodiment, the distal end first staple array 19a and the proximal end first staple array 19c are arranged in two rows or more in a direction perpendicular to a direction in which the groove portion 22 extends and along the first grasping surface 17. The distal end first staple array 19a and the proximal end first staple array 19c are arranged in the direction in which the groove portion 22 extends and in a state in which the arrays surround the preservation region A3 leaving gaps therebetween.

The distal end second staple array 19b and the proximal end second staple array 19d are constituted by the plurality of staples 27 arranged in the direction in which the groove portion 22 extends. In the embodiment, the distal end second staple array 19b and the proximal end second staple array 19d are arranged in two rows or more in a direction perpendicular to the direction in which the groove portion 22 extends and along the first grasping surface 17. The distal end second staple array 19b and the proximal end second staple array 19d are arranged in the direction in which the groove portion 22 extends and in a state in which the arrays surround the preservation region A3 leaving gaps therebetween.

Accordingly, the staple arrays 19 have the plurality of staples 27 that can be shot from the first jaw 10 toward the second jaw 50, which is disposed around the groove portion 22.

As shown in FIGS. 3, 4 and 5, the groove portion 22 is a linear groove in which the first dissecting knife 35 (to be described below) of the actuation part 31 is housed to be able to advance and retreat. In the embodiment, the groove portion 22 has a straight shape. The groove portion 22 defines a separating line L during separation of the tissue. In the embodiment, the separating line L has a straight shape parallel to a longitudinal central axis of the first jaw 10.

As shown in FIGS. 2, 3 and 4, the groove portion 22 has a first wall surface 23 and a second wall surface 24 that are separated from each other, and a bottom surface 25 configured to connect the first wall surface 23 and the second wall surface 24. The groove portion 22 has a first groove portion 22a disposed at a distal end side of the first jaw 10, and a second groove portion 22b disposed at a proximal end side of the first jaw 10. Each of the first groove portion 22a and the second groove portion 22b has the first wall surface 23, the second wall surface 24 and the bottom surface 25, which were described above.

The first groove portion 22a shown in FIG. 2 defines a separation length of the tissue by the first dissecting knife 35 (to be described below). That is, the first groove portion 22a defines a length of the first dissecting part 55a measured in a longitudinal central axis direction of the first jaw 10. The length of the first dissecting part 55a measured along the longitudinal central axis direction of the first jaw 10 is larger than that of the second dissecting part 55b measured along the longitudinal central axis direction of the first jaw 10. In the embodiment, the length of the first groove portion 22a in the longitudinal central axis direction of the first jaw 10 may be a length such that a jaw of a known stapler can be inserted into an incision formed in living body tissue when the living body tissue is separated using the first dissecting knife 35 to continue cutting the living body tissue from the incision. Further, when the present embodiment is applied to a procedure in which cutting of the living body tissue need not continue from the incision formed at the living body tissue when the living body tissue is separated using the first dissecting knife 35 or a procedure in which separation of the tissue using the first dissecting knife 35 is not needed, the length of the first groove portion 22a in the longitudinal central axis direction of the first jaw 10 is not particularly limited.

The first groove portion 22a defines disposition of the first dissecting part 55a such that a joinable region (the first suture region A1) by the first joining part 54a is interposed between a tissue preservation part 56 and the first groove portion 22a.

The second groove portion 22b shown in FIG. 2 defines a separation length of the tissue by the second dissecting knife 39 (to be described below). That is, the second groove portion 22b defines the length of the second dissecting part 55b when the length is measured along the longitudinal central axis direction of the first jaw 10. The second groove portion 22b defines disposition of the second dissecting part 55b such that a joinable region (the second suture region A2) by the second joining part 54b is interposed between the tissue preservation part 56 and the second groove portion 22b. In the embodiment, the length of the second groove portion 22b in the longitudinal central axis direction of the first jaw 10 is set to correspond to the disposition of the housing portion 18 such that the second groove portion 22b is surrounded by the housing portion 18. Accordingly, leakage of a body liquid or the like cannot easily occur when a joining area joined using the second joining part 54b is separated using the second dissecting knife 39.

As shown in FIGS. 3 and 4, the bottom surface 25 of the groove portion 22 in the embodiment is constituted by a portion of an inner surface of the base section 11. Further, in the embodiment, in an intermediate region of the first jaw 10 in the direction in which the groove portion 22 extends, in order to allow passage of the actuation part 31, a gap is opened between the first wall surface 23 and the bottom surface 25 and a gap is opened between the second wall surface 24 and the bottom surface 25.

The first wall surface 23 has a surface crossing the first grasping surface 17 of the holder body portion 16. The first wall surface 23 extends from the first grasping surface 17 of the holder body portion 16 toward a bottom section of the concave portion 12 of the base section 11. The first wall surface 23 extends in a longitudinal axis direction of the base section 11.

The second wall surface 24 is a surface disposed in parallel (including substantially in parallel) to the first wall surface 23 at a position separated from the first wall surface 23 by a distance through which the first dissecting knife 35 of the actuation part 31 can pass. The second wall surface 24 is a surface crossing the first grasping surface 17 of the holder body portion 16. The second wall surface 24 extends from the first grasping surface 17 of the holder body portion 16 toward the bottom section of the concave portion 12 of the base section 11. The second wall surface 24 extends in the longitudinal axis direction of the base section 11.

The driver 26 is disposed in the housing portion 18. The driver 26 is movable in the housing portion 18 by the first cam 33 of the actuation part 31. That is, when the driver 26 is moved toward an opening of the first grasping surface 17 side in the housing portion 18 by the first cam 33, the driver 26 presses a connecting portion 30 of the staples 27 toward the opening of the first grasping surface 17 side, and the staples 27 are pushed out of the housing portion 18.

The staples 27 are members configured to join the living body tissue and coupled to the living body.

Figure 18:
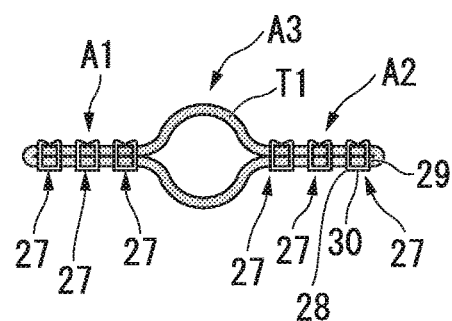
FIG. 18 is a cross-sectional view showing the alimentary canal joined in laparoscopic cardioplasty using the surgical instrument of the embodiment.

For example, as shown in FIG. 18, each of the staples 27 has a pair of leg sections 28 and 29 having insertion ends that are configured to be inserted into the tissue, and the connecting portion 30 connect the pair of leg sections 28 and 29. The staple 27 is formed in a fl shape (a U shape in which all corners are right angles) by bending a deformable and biocompatible wire material. A known structure may be appropriately selected and employed for the shape of the staple 27.

As shown in FIG. 2, the actuation part 31 has a first actuation part 32 disposed in the vicinity of the distal end portion of the first jaw 10, and a second actuation part 36 disposed in the vicinity of the proximal end portion of the first jaw 10.

As shown in FIGS. 2, 3 and 6, the first actuation part 32 is operated to perform joining of the living body tissue pinched between the first jaw 10 and the second jaw 50 in the vicinity of the distal end portion of the first jaw 10 and separation of a joined portion in the living body tissue. The first actuation part 32 has the first cam 33 and the first dissecting knife 35.

As shown in FIG. 3, the first cam 33 is disposed in the base section 11 to move the driver 26 to push the staples 27 included in the first suture region A1 out of the housing portion 18. As shown in FIG. 6, the first cam 33 is connected to the distal end of the second connecting member 5b of the connecting member 5, and can be moved by moving the second connecting member 5b in a central axis direction thereof. The first cam 33 has an inclined surface 34 inclined with respect to the longitudinal axis of the base section 11. The inclined surface 34 of the first cam 33 comes in contact with the driver 26 to move the driver 26 when the first cam 33 is moved from the distal end side toward the proximal end side in the longitudinal axis direction of the base section 11. A moving direction of the first cam 33 is a direction in which the groove portion 22 extends (see FIG. 2).

Figure 14:
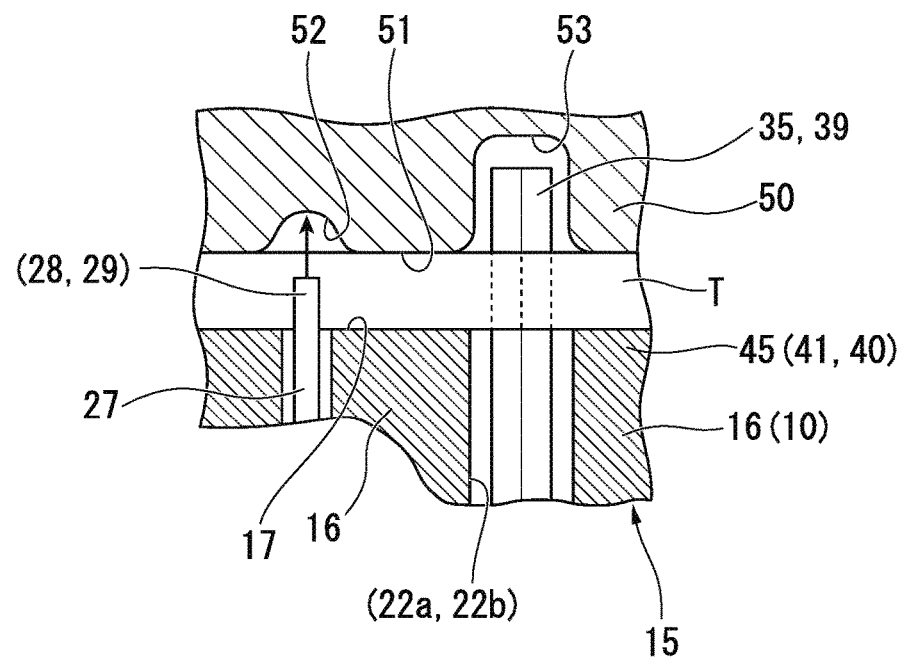
FIG. 14 is a view showing a process of suture serving as an example of joining in the surgical instrument.

The first dissecting knife 35 shown in FIG. 6 has a blade that can be operated independently from the first cam 33. The first dissecting knife 35 has a sharp structure formed at the proximal end thereof that can separate the tissue of the living body. The first dissecting knife 35 is disposed at the first groove portion 22a (see FIG. 2) to protrude from the first grasping surface 17 toward the second jaw 50. As shown in FIGS. 2 and 14, a protrusion amount of the first dissecting knife 35 from the first grasping surface 17 is a protrusion amount at which the first dissecting knife 35 is not hooked on the second grasping surface 51 of the second jaw 50 when the first jaw 10 and the second jaw 50 are in a closed state.

The first dissecting knife 35 can cut the living body tissue pinched between the first jaw 10 and the second jaw 50 in a process of moving the knife from the distal end side to the proximal end side of the first jaw 10.

The second actuation part 36 shown in FIGS. 2, 4 and 7 is operated to perform joining of the living body tissue pinched between the first jaw 10 and the second jaw 50 in the vicinity of the proximal end portion of the first jaw 10 and separation of the joined portion in the living body tissue. The second actuation part 36 has the second cam 37 and the second dissecting knife 39.

As shown in FIG. 4, the second cam 37 is disposed in the base section 11 to move the driver 26 to push the staples 27 included in the second suture region A2 out of the housing portion 18. As shown in FIG. 7, the second cam 37 is connected to the distal end of the third connecting member 5c of the connecting member 5, and is can be moved by moving the third connecting member 5c in the central axis direction. The second cam 37 has an inclined surface 38 inclined with respect to the longitudinal axis of the base section 11. The inclined surface 38 of the second cam 37 comes in contact with the driver 26 to move the driver 26 when the second cam 37 is moved from the proximal end side toward the distal end side in the longitudinal axis direction of the base section 11. A moving direction of the second cam 37 is a direction in which the groove portion 22 extends (see FIG. 2).

The second dissecting knife 39 shown in FIG. 7 has a blade that can be operated independently from the second cam 37. The second dissecting knife 39 has a sharp structure at the distal end thereof that can separate the tissue of the living body. The second dissecting knife 39 is disposed in the second groove portion 22b to protrude from the first grasping surface 17 toward the second jaw 50 (see FIG. 14). A protrusion amount of the first dissecting knife 35 from the first grasping surface 17 is a protrusion amount at which the second dissecting knife 39 is not hooked on the second grasping surface 51 of the second jaw 50 when the first jaw 10 and the second jaw 50 are in a closed state.

The second dissecting knife 39 can cut the living body tissue pinched between the first jaw 10 and the second jaw 50 in a process in which the knife is moved from the proximal end side toward the distal end side of the first jaw 10.

As shown in FIG. 8, the second jaw 50 has the second grasping surface 51 in which a plurality of forming pockets 52 are formed.

As shown in FIG. 2, the second grasping surface 51 is a surface directed toward the first grasping surface 17 of the first jaw 10. When the first jaw 10 is closed with respect to the second jaw 50, a distance between the first grasping surface 17 of the first jaw 10 and the second grasping surface 51 of the second jaw 50 is previously set depending on a thickness of the tissue serving as a suture target (see FIG. 14). The distance between the first grasping surface 17 of the first jaw 10 and the second grasping surface 51 of the second jaw 50 is a distance at which conglutination of the tissue serving as a suture target after suture using the staples 27 can easily occur, and excessive detrition of the tissue serving as the suture target cannot easily occur.

As shown in FIG. 8, the forming pockets 52 and a clearance groove 53 into which the protruding end of the first dissecting knife 35 can enter and that are elongated in the longitudinal axis direction of the second jaw 50 are formed at the second grasping surface 51.

The forming pockets 52 shown in FIG. 8 have inclined surfaces or curved surfaces configured to guide the leg sections 28 and 29 to plastically deform the leg sections 28 and 29 (see FIG. 18) of the staples 27 such that the tissue is sutured. In the embodiment, the plurality of forming pockets 52 are disposed at areas corresponding to the first suture region A1 and the second suture region A2. The forming pockets 52 may not be disposed at the areas corresponding to the preservation region A3.

As shown in FIG. 8, the clearance groove 53 has a first clearance groove 53a recessed from the second grasping surface 51 to ensure separation of the tissue by the first dissecting knife 35, and a second clearance groove 53b recessed from the second grasping surface 51 to ensure separation of the tissue by the second dissecting knife 39.

As shown in FIGS. 2 and 3, in the embodiment, the first joining part 54a configured to join the living body tissue by suturing the living body tissue according to operation of a operation section 63 (see FIG. 1) is constituted by the holder body portion 16 having the housing portion 18, the first cam 33, the driver 26 and the staples 27.

As shown in FIGS. 2 and 4, in the embodiment, the second joining part 54b configured to join the living body tissue by suturing the living body tissue according to operation of the operation section 63 (see FIG. 1) is constituted by the holder body portion 16 having the housing portion 18, the second cam 37, the driver 26 and the staples 27.

The first joining part 54a and the second joining part 54b constitute a stapling mechanism configured to conglutinate a plurality of tissues using the staples 27 in a state in which the plurality of tissues that are separated from each other are grasped by the first jaw 10 and the second jaw 50.

As shown in FIGS. 2 and 3, in the embodiment, a tissue separating structure of the first dissecting part 55a configured to cut the living body tissue according to operation of the operation section 63 (see FIG. 1) is constituted by the holder body portion 16 having the first groove portion 22a and the first dissecting knife 35.

As shown in FIGS. 2 and 4, in the embodiment, a tissue separating structure of the second dissecting part 55b configured to cut the living body tissue according to operation of the operation section 63 (see FIG. 1) is constituted by the holder body portion 16 having the second groove portion 22b and the second dissecting knife 39.

As shown in FIG. 5, in the embodiment, a space between the first joining part 54a and the second joining part 54b and a space between the first dissecting part 55a and the second dissecting part 55b become the tissue preservation parts 56 in which the living body tissue remains in a non-joined and non-separated state.

The stapler 60 shown in FIG. 1 has the shaft 61 having an elongated tubular shape, the operation section 63 connected to the proximal end of the shaft 61, and the transmission member 71 disposed in the operation section 63 and the shaft 61.

The proximal end of the shaft section 3 of the cartridge 2 is attachable to the distal end of the shaft 61. In the embodiment, an insertion section 62 of the surgical instrument 1 that can be inserted into the body is constituted by the cartridge 2 and the shaft 61 of the stapler 60.

The operation section 63 is disposed at the proximal end of the shaft 61 for a user to perform operation of opening/closing the first jaw 10 and the second jaw 50, attaching the staples 27 to the tissue and further separating the tissue.

The operation section 63 has a barrel 64 fixed to the proximal end of the shaft 61 and a handle section 65 connected to the barrel 64.

The barrel 64 is fixed to the proximal end of the shaft 61 in order for a user to rotate the shaft 61 about a central axis of the shaft 61 serving as a rotational center.

The handle section 65 has a main body portion 66, a fixing handle 67, a movable handle 68 (an opening/closing operation part) for an opening/closing operation, a movable handle 69 (a joining operation part, a separating operation part) for a joining/separating operation, and a fixing part 70.

The main body portion 66 is rotatably connected to the barrel 64 about a central axis of the shaft 61 serving as a rotational center.

The fixing handle 67 has substantially a rod shape extending from the main body portion 66. The fixing handle 67 is a portion that a user's hand grasps.

The movable handle 68 for the opening/closing operation is a handle configured to operate opening/closing of the first jaw 10 with respect to the second jaw 50. The movable handle 68 for the opening/closing operation is biased in one direction by a biasing member (for example, a spring), which is not shown, such that the first jaw 10 is in an opened state with respect to the second jaw 50. When an operator moves the movable handle 68 for the opening/closing operation against a biasing force of a biasing member configured to bias the movable handle 68 for the opening/closing operation, the first jaw 10 can be closed with respect to the second jaw 50.

The movable handle 68 for the opening/closing operation is connected to the first transmission member 71a (to be described below).

The movable handle 69 for the joining/separating operation has a plurality of handle members (a first joining operation handle 69a, a second joining operation handle 69b, a first separation operation handle 69c and a second separation operation handle 69d) disposed at the fixing handle 67. While disposition of the plurality of handle members is not particularly limited, in the embodiment, the handle members are disposed in a row in a longitudinal direction of the fixing handle 67 such that the first joining operation handle 69a can be manipulated by an index finger of the operator, the second joining operation handle 69b can be manipulated by a middle finger of the operator, the first separation operation handle 69c can be manipulated by a ring finger of the operator, and the second separation operation handle 69d can be manipulated by a little finger of the operator.

The first joining operation handle 69a and the second joining operation handle 69b are joining operation parts configured to join the living body tissue.

The first joining operation handle 69a is connected to the fixing handle 67 to be movable with respect to the fixing handle 67 to perform a joining operation using the first joining part 54a. The first joining operation handle 69a is connected to the second transmission member 71b (to be described below).

The second joining operation handle 69b is connected to the fixing handle 67 to be movable with respect to the fixing handle 67 to perform a joining operation using the second joining part 54b. The second joining operation handle 69b is connected to the third transmission member 71c (to be described below).

The first separation operation handle 69c and the second separation operation handle 69d are separating operation parts configured to cut the living body tissue.

The first separation operation handle 69c is connected to the fixing handle 67 to be movable with respect to the fixing handle 67 to perform a separating operation using the first dissecting part 55a. The first separation operation handle 69c is connected to the fourth transmission member 71d (to be described below).

The second separation operation handle 69d is connected to the fixing handle 67 to be movable with respect to the fixing handle 67 to perform a separating operation using the second dissecting part 55b. The second separation operation handle 69d is connected to the fifth transmission member 71e (to be described below).

When the first joining operation handle 69a, the second joining operation handle 69b, the first separation operation handle 69c and the second separation operation handle 69d are simultaneously operated with the fingers of the operator hooked on all of the handles, the first joining part 54a, the second joining part 54b, the first dissecting part 55a and the second dissecting part 55b can be manipulated by a single grasping operation of a hand.

When all of the first joining operation handle 69a, the second joining operation handle 69b, the first separation operation handle 69c and the second separation operation handle 69d are manipulated, as shown in FIG. 10, joining by suture of the living body tissue T and separation of the living body tissue T are respectively performed in the first suture region A1 and the second suture region A2.

In addition, the first joining operation handle 69a, the second joining operation handle 69b, the first separation operation handle 69c and the second separation operation handle 69d may be arbitrarily selected to be manipulated individually or in combination with each other according to necessity.

For example, in the procedure in which the joining of the living body tissue is performed but the separation of the living body tissue is not required, by manipulating the first joining operation handle 69a and the second joining operation handle 69b and not manipulating the first separation operation handle 69c and the second separation operation handle 69d, as shown in FIG. 11, only the joining of the living body tissue T is performed in each of the first suture region A1 and the second suture region A2.

In addition, as a separate example, for example, in the procedure in which the joining of the living body tissue using the first joining part 54a and the second joining part 54b and the separation of the living body tissue in the first joining region A1 using the first dissecting part 55a are required, by manipulating the first joining operation handle 69a, the second joining operation handle 69b and the first separation operation handle 69c and not manipulating the second separation operation handle 69d, as shown in FIG. 12, the joining of the living body tissue T is performed in each of the first suture region A1 and the second suture region A2, and further the separation of the tissue in the first joining region A1 are performed.

The fixing part 70 shown in FIG. 1 is disposed at the main body portion 66 to fix the first jaw 10 which is operated by the movable handle 68 for the opening/closing operation in the closed state in which the first jaw 10 is positioned close to the second jaw 50. The fixing part 70 switches a state in which the first jaw 10 is relatively movable with respect to the second jaw 50 and a state in which the first jaw 10 is fixed to the second jaw 50 relatively immovably according to operation by the user.

The transmission members 71 (the first transmission member 71a, the second transmission member 71b, the third transmission member 71c, the fourth transmission member 71d and the fifth transmission member 71e) are members configured to transmit the operation of the movable handle 68 for the opening/closing operation and the movable handle 69 for the joining/separating operation from the operation section 63 to the cartridge 2.

The first transmission member 71a is a rod-shaped member configured to connect the movable handle 68 for the opening/closing operation and the first connecting member 5a.

The second transmission member 71b is a rod-shaped member configured to connect the first joining operation handle 69a and the second connecting member 5b.

The third transmission member 71c is a rod-shaped member configured to connect the second joining operation handle 69b and the third connecting member 5c.

The fourth transmission member 71d is a rod-shaped member configured to connect the first separation operation handle 69c and the fourth connecting member 5d.

The fifth transmission member 71e is a rod-shaped member configured to connect the second separation operation handle 69d and the fifth connecting member 5e.

A known configuration may be appropriately selected as a configuration of the transmission member 71 to correspond to a direction and a magnitude of a force that is transmitted from the movable handle 69 toward the cartridge 2 via the transmission member 71. For example, a rod, a wire, a link, or the like may be used as a component of the transmission member 71.

Figure 13:
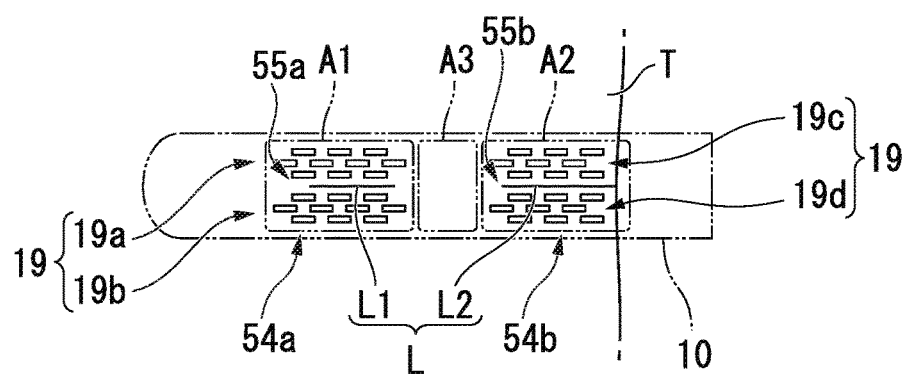
FIG. 13 is a schematic view showing a state in which a joining region and a separating line in living body tissue are confirmed using the surgical instrument.

Next, an action of the surgical instrument 1 of the embodiment will be described. FIG. 13 is a schematic view showing a state in which a joining region and a separating line are confirmed in the living body tissue using the surgical instrument of the embodiment. FIG. 14 is a view showing a process of suture serving as an example of joining in the surgical instrument of the embodiment.

The surgical instrument 1 is prepared in a state in which, as shown in FIGS. 3 and 4, the staples 27 are housed in the housing portion 18, and as shown in FIG. 2, the first cam 33 and the first dissecting knife 35 are disposed in the vicinity of the distal end of the base section 11 and the second cam 37 and the second dissecting knife 39 are disposed in the vicinity of the proximal end of the base section 11.

When the surgical instrument 1 is used, the surgical instrument 1 is guided to a treatment target area through, for example, a trocar, by a known procedure.

The first jaw 10 and the second jaw 50 disposed at the distal end portion of the insertion section 62 of the surgical instrument 1 grasp the living body tissue T serving as a joining or separating target as shown in FIG. 9 according to operation of the movable handle 68 for the opening/closing operation of the operation section 63 under observation of a laparoscope (not shown).

When the living body tissue T serving as the joining or separating target is grasped by the first jaw 10 and the second jaw 50, the first suture region A1 and the second suture region A2 configured to attach the staples 27, the preservation region A3 configured to preserve the living body tissue between the first suture region A1 and the second suture region A2, and the separating lines L (the first separating line L1 and the second separating line L2) are defined in the living body tissue T of the joining or separating target as shown in FIG. 13.

The first separating line L1 and the second separating line L2 are disposed at the same straight line and separated from each other with the preservation region A3 sandwiched therebetween. In addition, the first separating line L1 is disposed inside the first suture region A1, and the first separating line L1 is surrounded by the staples 27. In addition, the second separating line L2 is disposed inside the second suture region A2, and the second separating line L1 is surrounded by the staples 27. For this reason, either the first separating line L1 or the second separating line L2 can be joined by the staples 27 such that leakage of liquid or the like does not occur.

A user of the surgical instrument 1 fixes a position of the first jaw 10 with respect to the second jaw 50 in a state in which the first jaw 10 and the second jaw 50 grasp the tissue by manipulating the fixing part 70 of the operation section 63 shown in FIG. 1 and fixing the movable handle 68 for the opening/closing operation of the main body portion 66 of the operation section 63. When the position of the first jaw 10 with respect to the second jaw 50 is fixed, the first suture region A1, the second suture region A2, the preservation region A3, the first separating line L1 and the second separating line L2 are confirmed in a state shown in FIG. 13.

The user performs operation on the movable handle 69 for the joining/separating operation after fixing the movable handle 68 for the opening/closing operation to the main body portion 66 using the fixing part 70.

For example, the first cam 33 is moved from the distal end side toward the proximal end side via the second transmission member 71b and the second connecting member 5b by operation of the first joining operation handle 69a. The first cam 33 (see FIG. 3) moved toward the proximal end side raises the driver 26 along the inclined surface 34. As the driver 26 is raised by the inclined surface 34, the driver 26 pushes the staples 27 out of the housing portion 18 such that insertion ends of the staples 27 pierce the tissue. In addition, in the distal end portion of the first groove portion 22a, leakage of the liquid or the like when the tissue is separated in the first groove portion 22a is prevented by shooting the plurality of staples 27 to surround the distal end of the first groove portion 22a.

When the staples 27 are pushed out of the housing portion 18, the leg sections 28 and 29 of the staples 27 abut the forming pockets 52 as shown in FIG. 14. The forming pockets 52 deform the leg sections 28 and 29 of the staples 27 into a predetermined shape for suturing the tissue.

The staples 27 are sequentially shot from the housing portion 18 according to movement of the first cam 33 from the distal end toward the proximal side of the first jaw 10 to the proximal end portion of the first groove portion 22a. In addition, in the proximal end portion of the first groove portion 22a, leakage of the liquid or the like when the tissue is separated along the first groove portion 22a is prevented by shooting the plurality of staples 27 to surround the proximal end of the first groove portion 22a.

In this way, the first joining part 54a sutures the tissue grasped by the first jaw 10 and the second jaw 50 using the staples 27. In the embodiment, the living body tissue to which the staples 27 are attached is irreversibly joined in an adhesible state by suturing the living body tissue using the staples 27. Further, after attachment of the staples 27, the staples 27 can be removed from the living body tissue before the living body tissues are conglutinated.

Next, for example, the second cam 37 is moved from the proximal end side toward the distal end side via the third transmission member 71c and the third connecting member 5c by operation of the second joining operation handle 69b. Like the first cam 33, the second cam 37 pushes the staples 27 out of the housing portion 18 via the driver 26 using the inclined surface 38 of the second cam 37. The second cam 37 sequentially shoots the staples 27 disposed at the second suture region A2 from the proximal end side toward the distal end side to the distal end portion of the second groove portion 22b. In the second suture region A2, like the first suture region A1, as the plurality of staples 27 are shot to surround the proximal end and the distal end of the second groove portion 22b, leakage of the liquid or the like when the tissue is separated in the second groove portion 22b is prevented.

In this way, the second joining part 54b sutures the tissue grasped by the first jaw 10 and the second jaw 50 using the staples 27. In the embodiment, the living body tissue to which the staples 27 are attached is irreversibly joined in an adhesible state as the tissue is sutured using the staples 27.

Next, for example, the first dissecting knife 35 is moved from the distal end side toward the proximal end side via the fourth transmission member 71d and the fourth connecting member 5d by operation of the first separation operation handle 69c. The first dissecting knife 35 separates the living body tissue T pinched between the first jaw 10 and the second jaw 50 along the first separating line L1 defined by the first groove portion 22a in the first suture region A1 shown in FIG. 13.

Next, for example, the second dissecting knife 39 is moved from the proximal end side toward the distal end side via the fifth transmission member 71e and the fifth connecting member 5e by operation of the second separation operation handle 69d. The second dissecting knife 39 separates the living body tissue T pinched between the first jaw 10 and the second jaw 50 along the second separating line L2 defined by the second groove portion 22b in the second suture region A2 shown in FIG. 13.

Performance of suture in the first suture region A1, suture in the second suture region A2, separation along the first separating line L1 in the first suture region A1, and separation along the second separating line L2 in the second suture region A2 may be arbitrarily selected or combined formed.

For example, when the suture in the first suture region A1 and the suture in the second suture region A2 are performed, two places separated to sandwich the preservation region A3 therebetween are sutured (see FIG. 11).

In addition, when the separation along the first separating line L1 in the first suture region A1 and the separation along the second separating line L2 in the second suture region A2 are performed, two places separated to sandwich the preservation region A3 therebetween are separated on the same straight line.

In addition, when the suture in the first suture region A1, the suture in the second suture region A2 and the separation along the first separating line L1 in the first suture region A1 are performed, two places separated to sandwich the preservation region A3 therebetween are sutured, and a throughhole surrounded by the staples 27 is disposed at the first suture region A1 (see FIG. 10).

When the joining or separation of the living body tissue pinched between the first jaw 10 and the second jaw 50 is performed, the fixing part 70 shown in FIG. 1 is manipulated to make the first jaw 10 movable with respect to the second jaw 50 and the first jaw 10 is opened with respect to the second jaw 50, and the living body tissue on which the joining or separation is performed is removed from the surgical instrument 1.

As described above, according to the surgical instrument 1 of the embodiment, in a state in which the tissues separated from each other are pinched by the first jaw 10 and the second jaw 50, areas separated to correspond to the first suture region A1 and the second suture region A2 separated to sandwich the preservation region A3 therebetween can be joined or separated. Further, the joining or separation in the first suture region A1 and the second suture region A2 can be performed by simply selecting and manipulating a desired handle from the movable handle 69 for the joining/ separating operation in the operation section 63. In addition, since all or a plurality of the movable handles 69 for the joining/separating operation, which are arbitrarily selected, are easily simultaneously manipulated in the surgical instrument 1 of the embodiment, the joining and separating in the first suture region A1 and the joining and separating in the second suture region A2 can be arbitrarily combined and easily performed.

Next, several examples of a specific procedure using the surgical instrument 1 of the embodiment shown in FIGS. 1 to 14 will be described.

(Procedure 1. Laparoscopic Cardioplasty)

Figure 15:
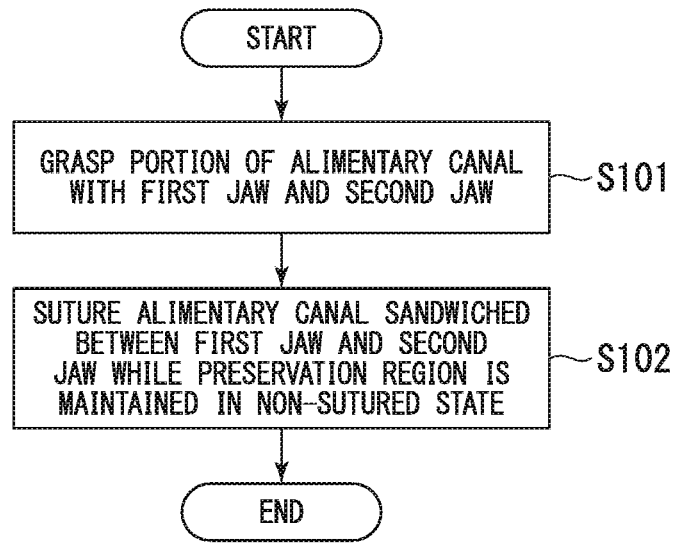
FIG. 15 is a flowchart showing a sequence of laparoscopic cardioplasty using the surgical instrument of the embodiment.
Figure 16:
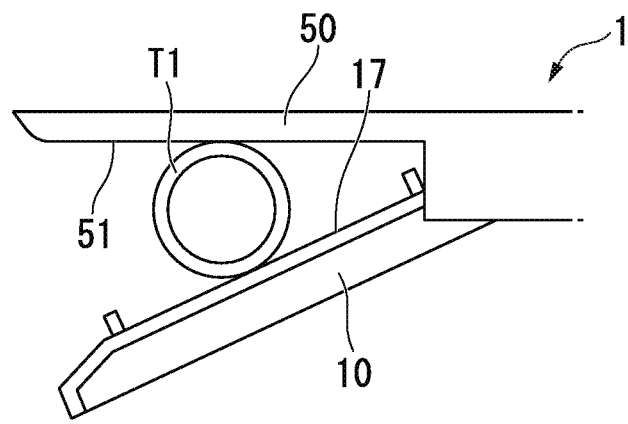
FIG. 16 is a view showing a state in which the surgical instrument approaches the alimentary canal in laparoscopic cardioplasty using the surgical instrument of the embodiment.
Figure 17:
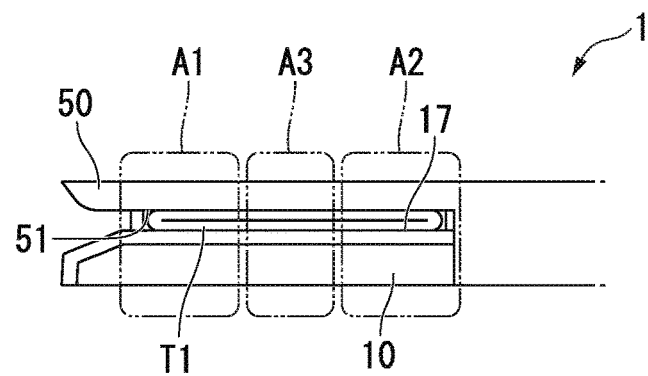
FIG. 17 is a view showing a grasping and joining state of the alimentary canal in laparoscopic cardioplasty using the surgical instrument of the embodiment.
Figure 19:
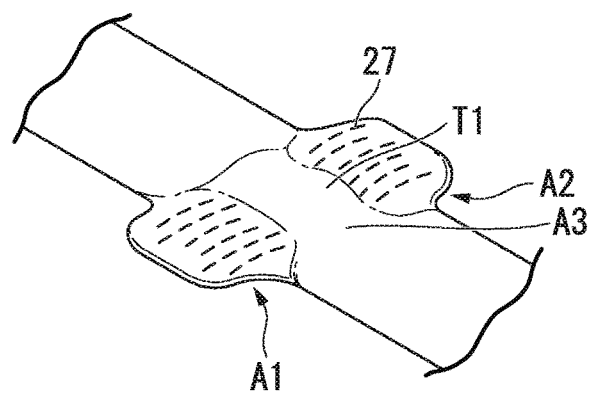
FIG. 19 is a perspective view showing the alimentary canal joined in laparoscopic cardioplasty using the surgical instrument of the embodiment.

An example of a specific procedure in the case in which two places separated a predetermined gap in the living body tissue are joined using the surgical instrument 1 is disclosed. FIG. 15 is a flowchart showing a sequence of laparoscopic cardioplasty using the surgical instrument of the embodiment. FIG. 16 is a view showing a state in which the surgical instrument approaches the alimentary canal in laparoscopic cardioplasty using the surgical instrument of the embodiment. FIG. 17 is a view showing a grasping and joining state of the alimentary canal in laparoscopic cardioplasty using the surgical instrument of the embodiment. FIG. 18 is a cross-sectional view showing the alimentary canal joined in laparoscopic cardioplasty using the surgical instrument of the embodiment. FIG. 19 is a perspective view showing the alimentary canal joined in laparoscopic cardioplasty using the surgical instrument of the embodiment.

First, a person who performs laparoscopic cardioplasty attaches a trocar to the abdominal wall through microincision, and the surgical instrument 1 of the embodiment is guided into the abdominal cavity via the trocar.

The gastroesophageal joining part or a portion of the alimentary canal T1 in the vicinity of the esophagus is grasped by the first jaw 10 and the second jaw 50 of the surgical instrument 1 (see FIGS. 16 and 17). Here, an operator of the surgical instrument 1 appropriately performs adjustment of the position such that the longitudinal central axis of the first jaw 10 is directed in a direction substantially perpendicular to a central axis of the alimentary canal T1 and further the preservation region A3 is disposed at a substantially intermediate portion in a radial direction of the alimentary canal T1. In a state in which the alimentary canal T1 is appropriately grasped by the first jaw 10 and the second jaw 50, the alimentary canal T1 is grasped by the first jaw 10 and the second jaw 50 in a state in which the alimentary canal T1 is included in both of the first joining region A1 and the second joining region A2 (a grasping process, step S101, see FIG. 15).

In this way, when the alimentary canal T1 is appropriately grasped by the first jaw 10 and the second jaw 50, the first joining operation handle 69a and the second joining operation handle 69b are manipulated and the first separation operation handle 69c and the second separation operation handle 69d are not manipulated (a simultaneous joining (suture) process, step S102, see FIG. 15). In step S102, the staples 27 are shot from the housing portion 18 in the first joining part 54a and the second joining part 54b according to operation of the first joining operation handle 69a and the second joining operation handle 69b. Some of the staples 27 shot from the housing portion 18 suture the alimentary canal T1 pinched between the first grasping surface 17 of the first jaw 10 and the second grasping surface 51 of the second jaw 50 in a state in which the alimentary canal T1 is folded (see FIGS. 17 and 18).

At a termination of step S102, the alimentary canal T1 pinched between the first grasping surface 17 of the first jaw 10 and the second grasping surface 51 of the second jaw 50 is in a state in which the preservation region A3 is not sutured and the other portion is sutured as shown in FIGS. 18 and 19.

In the laparoscopic cardioplasty using the surgical instrument 1, a function of a lumen of the alimentary canal T1 is maintained by a portion defined by a length dimension of the preservation region A3 in the longitudinal central axis direction of the first jaw 10 with respect to the alimentary canal T1, and the other portion is joined. As a result, the alimentary canal T1 is formed to have a diameter reduced to be smaller than a diameter before suture.

In the laparoscopic cardioplasty using the surgical instrument 1, since a size of the portion serving as the lumen after suture is uniquely determined by the dimension of the preservation region A3 of the first jaw 10, a cardiac orifice is easily formed without necessity of adjusting the diameter of the alimentary canal T1 by performing the suture a plurality of times from a plurality of directions outside the alimentary canal T1.

Further, in the laparoscopic cardioplasty using the surgical instrument 1, two places separated to sandwich the central axis of the alimentary canal T1 therebetween can be sutured by one suture operation. For this reason, the two separating places can be sutured using the surgical instrument 1 from the direction from which the alimentary canal T1 can be most easily approached.

Further, in the laparoscopic cardioplasty using the surgical instrument 1, since the first suture region A1 and the second suture region A2 can be sutured in a state in which the alimentary canal T1 is pinched and grasped by the first jaw 10 and the second jaw 50, in comparison with the case in which flexible tissue of the alimentary canal T1 is grasped and sutured a plurality of times, precise suture can be easily performed.

Further, the above-mentioned procedure can be applied to a procedure other than the laparoscopic cardioplasty in which both ends of the two areas of the living body tissue are joined or separated in a state in which the luminal tissue is preserved between the two areas in a lumen state with respect to the two separated areas. For example, a procedure of joining or separating living body tissue around a blood vessel or the urinary duct without damage can be performed using the surgical instrument 1 of the embodiment.

(Procedure 2. Laparoscopic Roux-En Y Gastric Bypass)

A specific example in the case in which a bypass that can be used to pass through an endoscope to the duodenum after reconstruction is formed in the stomach using the surgical instrument 1 of the embodiment in a process of forming a pouch in the stomach of a patient who receives a Roux-en Y gastric bypass is shown.

Figure 20:
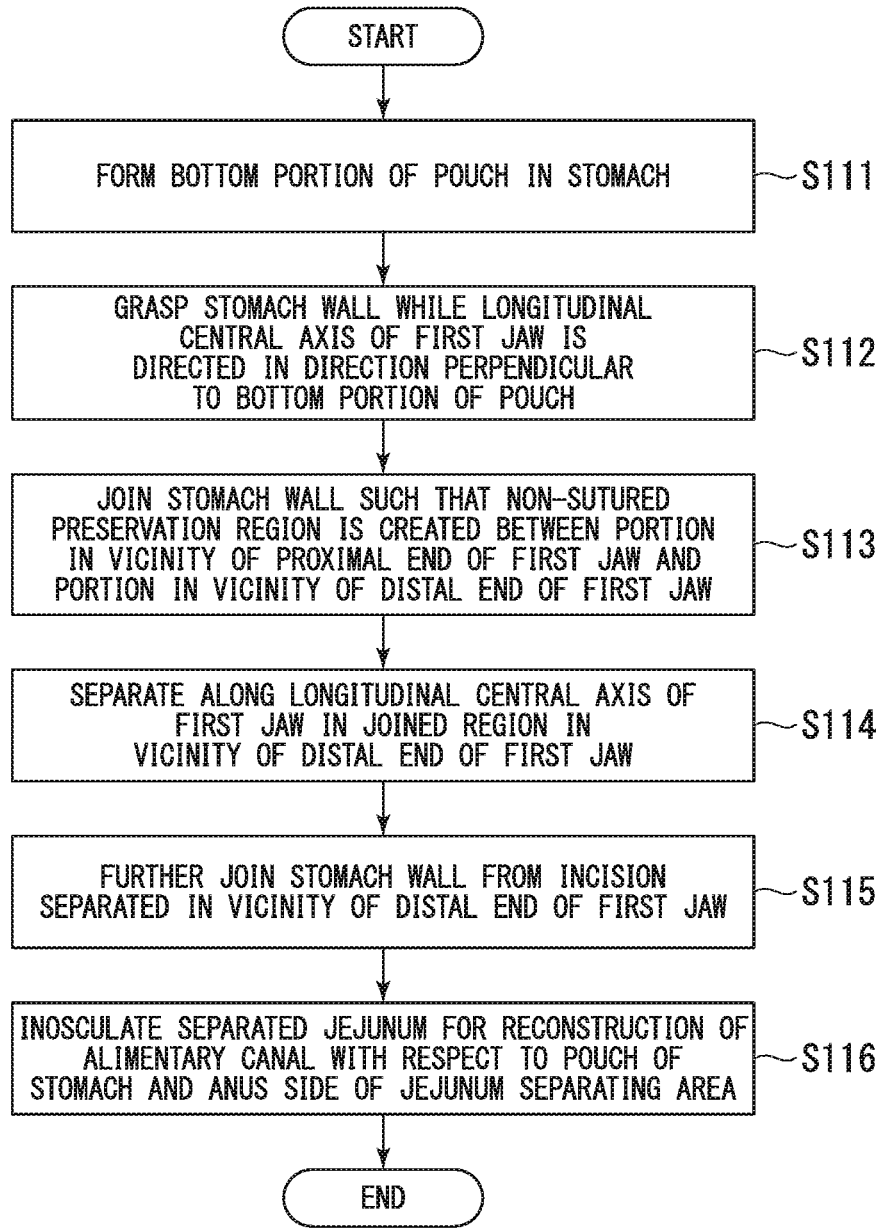
FIG. 20 is a flowchart showing a sequence of a laparoscopic Roux-en Y gastric bypass using the surgical instrument of the embodiment.
Figure 21:
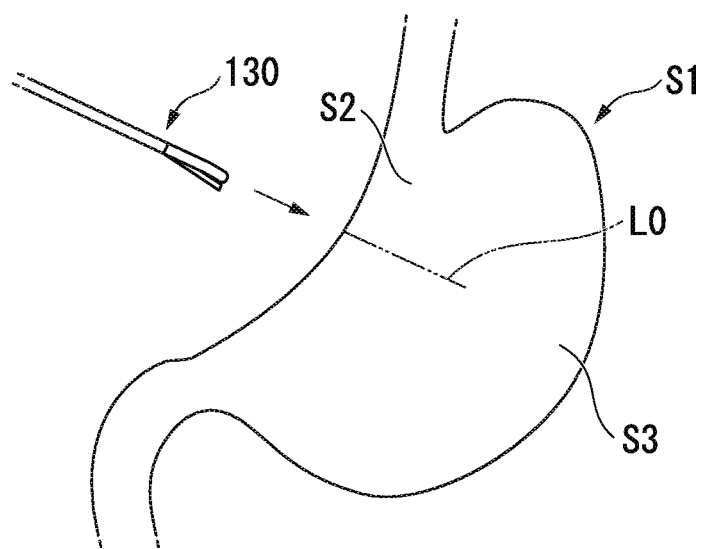
FIG. 21 is a schematic view showing a process of forming a pouch bottom section in a laparoscopic Roux-en Y gastric bypass using the surgical instrument of the embodiment.
Figure 22:
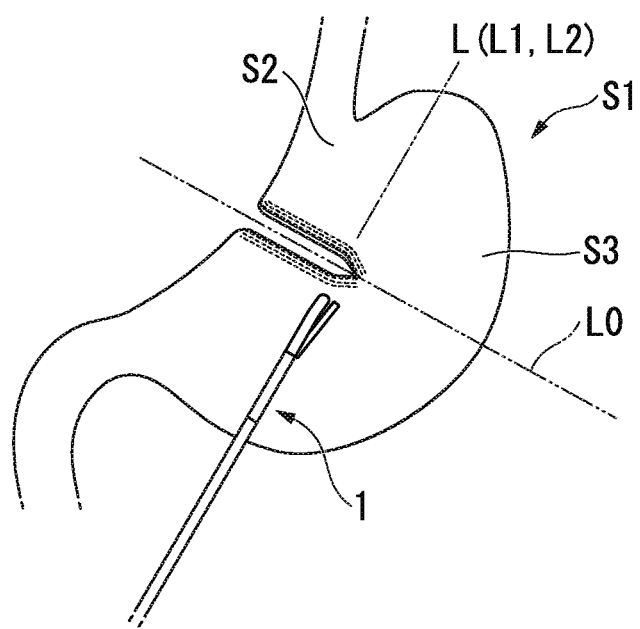
FIG. 22 is a schematic view showing a process of forming a bypass in a laparoscopic Roux-en Y gastric bypass using the surgical instrument of the embodiment.
Figure 23:
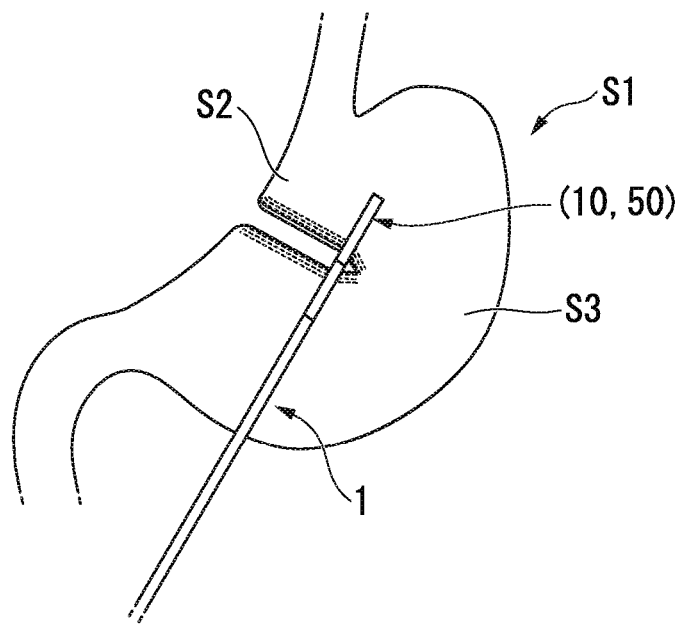
FIG. 23 is a schematic view showing a process of forming the bypass in a laparoscopic Roux-en Y gastric bypass using the surgical instrument of the embodiment.
Figure 24:
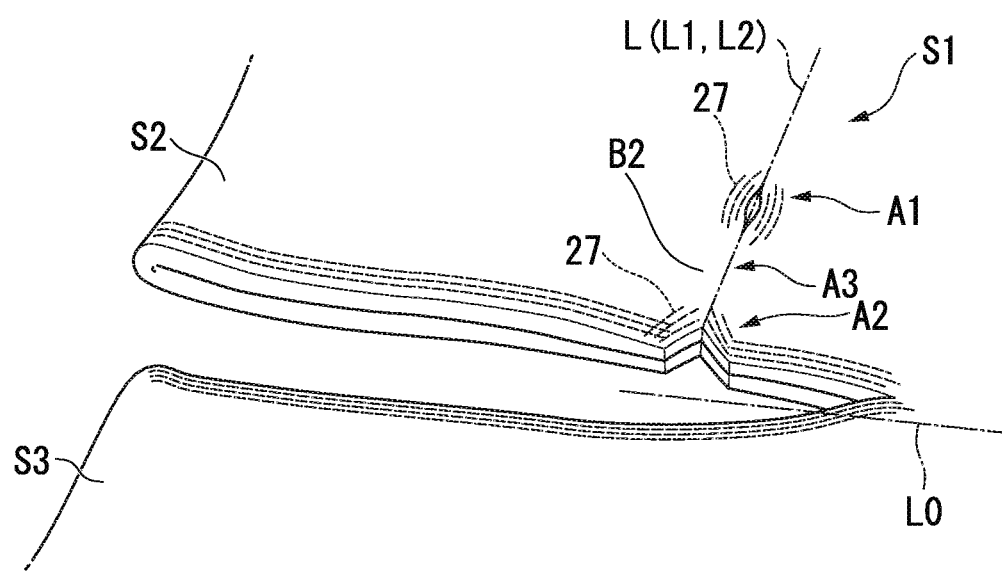
FIG. 24 is a schematic view showing the stomach after formation of the bypass in a laparoscopic Roux-en Y gastric bypass using the surgical instrument of the embodiment.
Figure 25:
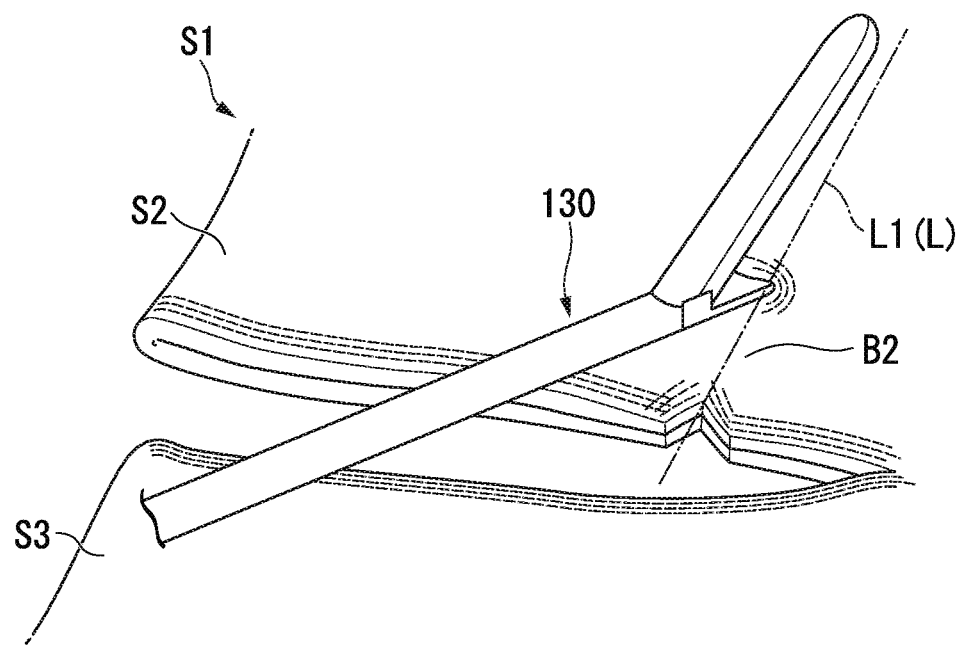
FIG. 25 is a schematic view showing a process of further continuing the joining and separating in the stomach after formation of the bypass in a laparoscopic Roux-en Y gastric bypass using the surgical instrument of the embodiment.
Figure 26:
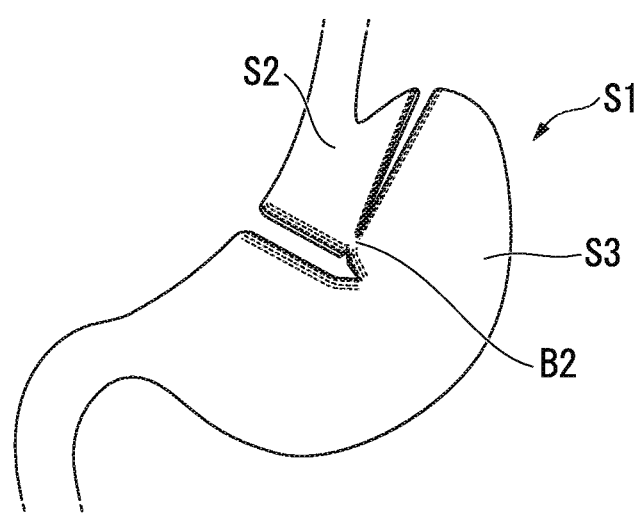
FIG. 26 is a schematic view showing a state in which the joining and separating are performed between a pouch and a remaining stomach in a laparoscopic Roux-en Y gastric bypass using the surgical instrument of the embodiment.
Figure 27:
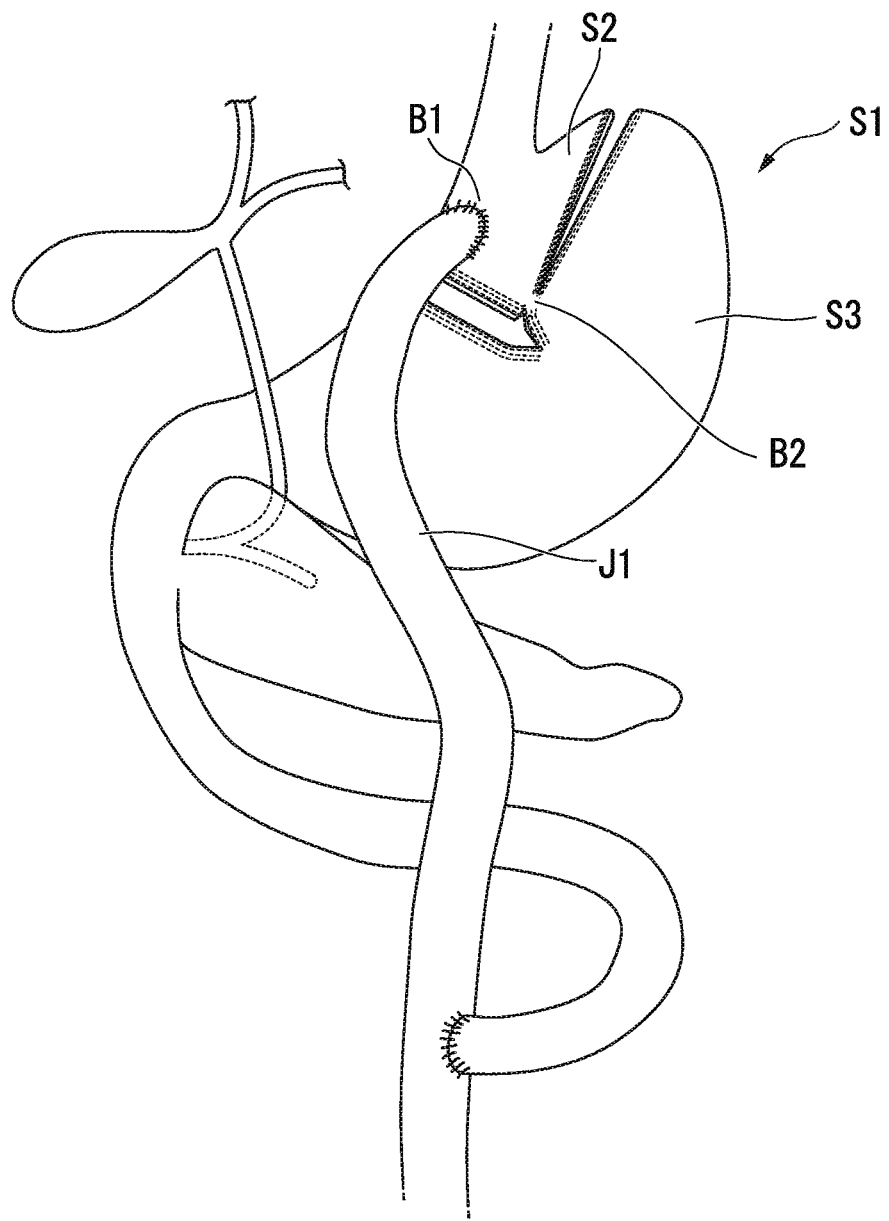
FIG. 27 is a schematic view showing an example of reconstruction of the alimentary canal after separation of the stomach in a laparoscopic Roux-en Y gastric bypass using the surgical instrument of the embodiment.
Figure 28:
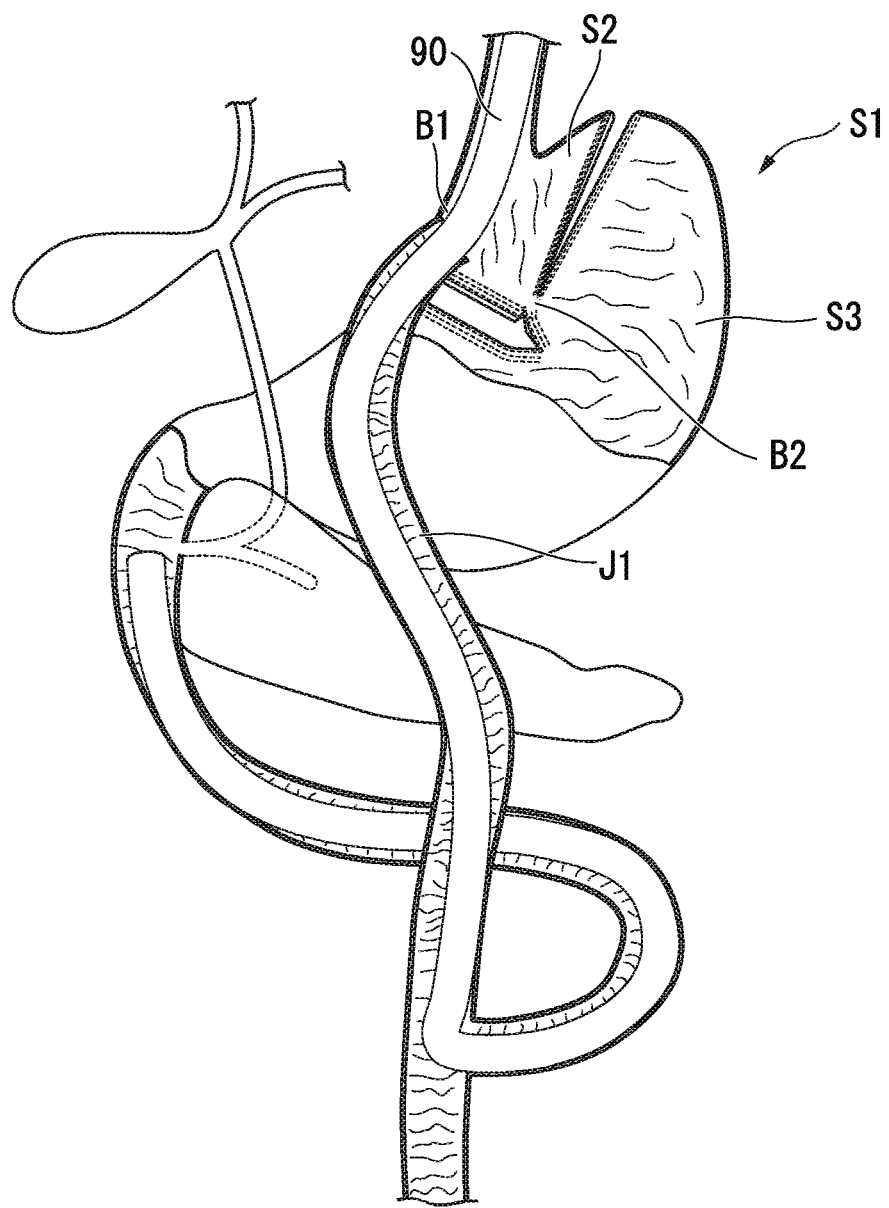
FIG. 28 is a schematic view showing an example of introducing an endoscope into the alimentary canal after separation of the stomach and reconstruction of the alimentary canal in a laparoscopic Roux-en Y gastric bypass using the surgical instrument of the embodiment.
Figure 29:
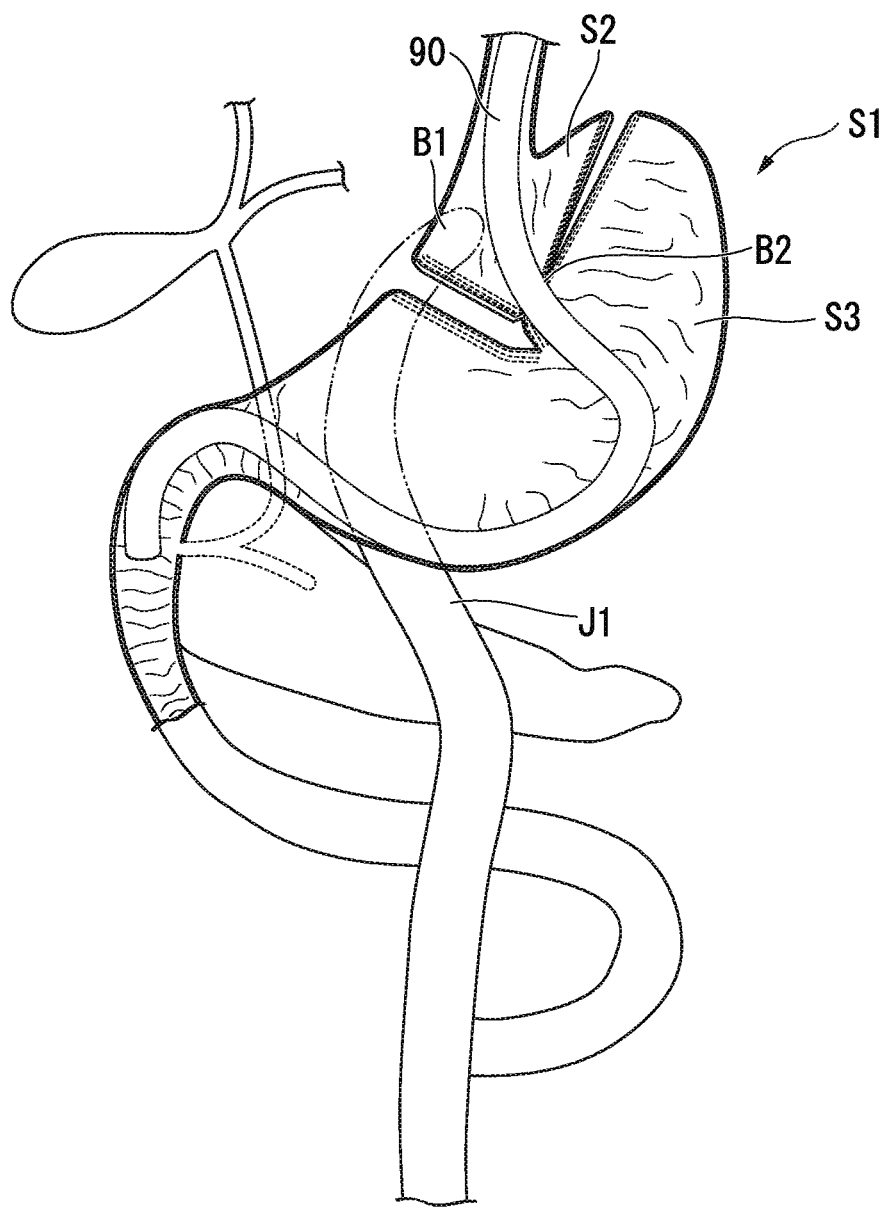
FIG. 29 is a schematic view showing an example of introducing an endoscope from the pouch into the duodenum through the bypass formed in the stomach using the surgical instrument of the embodiment.

FIG. 20 is a flowchart showing a sequence of a laparoscopic Roux-en Y gastric bypass using the surgical instrument of the embodiment. FIG. 21 is a schematic view showing a process of forming a pouch bottom section in a laparoscopic Roux-en Y gastric bypass using the surgical instrument of the embodiment. FIG. 22 is a schematic view showing a process of forming a bypass in a laparoscopic Roux-en Y gastric bypass using the surgical instrument of the embodiment. FIG. 23 is a schematic view showing a process of forming the bypass in a laparoscopic Roux-en Y gastric bypass using the surgical instrument of the embodiment. FIG. 24 is a schematic view showing the stomach after formation of the bypass in a laparoscopic Roux-en Y gastric bypass using the surgical instrument of the embodiment. FIG. 25 is a schematic view showing a process of continuing the joining and separating in the stomach after formation of the bypass in a laparoscopic Roux-en Y gastric bypass using the surgical instrument of the embodiment. FIG. 26 is a schematic view showing a state in which the joining and separating are performed between a pouch and a remaining stomach in a laparoscopic Roux-en Y gastric bypass using the surgical instrument of the embodiment. FIG. 27 is a schematic view showing an example of reconstruction of the alimentary canal after separation of the stomach in a laparoscopic Roux-en Y gastric bypass using the surgical instrument of the embodiment. FIG. 28 is a schematic view showing an example of introducing an endoscope into the alimentary canal after separation of the stomach and reconstruction of the alimentary canal in a laparoscopic Roux-en Y gastric bypass using the surgical instrument of the embodiment. FIG. 29 is a schematic view showing an example of introducing an endoscope from the pouch into the duodenum through the bypass formed in the stomach using the surgical instrument of the embodiment.

First, microincision is performed in the abdominal wall and the trocar is attached to the microincision, and medical instruments are introduced into the abdominal cavity via the trocar.

As shown in FIG. 21, in a process of forming a pouch S2 in the stomach S1, a known linear stapler 130 is first guided into the abdominal cavity and the linear stapler 130 is used via the trocar. Then, as shown in FIGS. 21 and 22, a bottom section of the pouch S2 is prepared using the linear stapler 130 as in the conventional method (a first joining separation process, step S111, see FIG. 20).

After step S111, the first jaw 10 and the second jaw 50 of the surgical instrument 1 of the embodiment are guided from the distal end of the separating line L0 (see FIG. 22) in step S111 in a direction substantially perpendicular to a separating line in step S111 (a direction substantially perpendicular to the bottom section of the pouch S2), and in a state in which the proximal end of the first jaw 10 is disposed in the vicinity of the distal end of the separating line L0 in step S111 and the longitudinal central axis of the first jaw 10 (the longitudinal central axis of the first jaw 10 of the embodiment is a straight line parallel to the separating line L of the surgical instrument 1) is directed in a direction substantially perpendicular to the bottom section of the pouch S2, the stomach S1 is grasped by the first jaw 10 and the second jaw 50 (a grasping process, step S112, see FIG. 20). In a state in which the stomach S1 is grasped by the first jaw 10 and the second jaw 50 in step S112 as shown in FIG. 23, the stomach wall is pinched between the first grasping surface 17 and the second grasping surface 51 in a state in which the inner walls of the stomach S1 come in contact with each other.

After step S112, the stomach walls are joined at a portion in the vicinity of the proximal end of the first jaw 10 and a portion in the vicinity of the distal end of the first jaw 10 such that the non-sutured preservation region A3 is created between the distal end and the proximal end of the first jaw 10 (a joining process, step S113, see FIG. 20). In the procedure using the surgical instrument 1 of the embodiment, as the staples 27 are shot from the housing portion 18 at both of the first suture region A1 and the second suture region A2 in the surgical instrument 1, a predetermined non-sutured portion defined by a shape of the preservation region A3 disposed between the first suture region A1 and the second suture region A2 of the surgical instrument 1 is provided, and both of the first suture region A1 and the second suture region A2 are joined by the suture using the staples 27. As shown in FIG. 24, the predetermined non-sutured portion defined by the shape of the preservation region A3 forms a lumen shape configured to connect the pouch S2 and the remaining stomach S3 by the first suture region A1 and the second suture region A2. The lumen-shaped portion is connected by the staples 27 such that a gastric fluid or food does not leak to the outside of the stomach and serves as a bypass B2 configured to connect the pouch S2 and a remaining stomach S3. The bypass B2 configured to connect the pouch S2 and the remaining stomach S3 can be used to pass through an endoscope 90 to the duodenum after reconstruction in a patient who receives the Roux-en Y gastric bypass.

After step S113, the joined living body tissue is separated while the stomach wall is grasped by the first jaw 10 and the second jaw 50 (a separation process, step S114, see FIG. 20). In step S114, separation along the longitudinal central axis direction of the first jaw 10 is performed at least in the first suture region A1 in the vicinity of the distal end of the first jaw 10, in the first suture region A1 and the second suture region A2 (see FIG. 24). The first suture region A1 of the stomach S1 is disposed at an opposite side with the bypass B2 in a non-joined state by the preservation region A3 with respect to the separating line L0 separated by the known linear stapler 130 in step S11. In addition, the first joining region A1 of the stomach S1 may be short in a region to be joined to complete the pouch S2 depending on the dimension of the first jaw 10, and in such a case, the stomach wall should be joined from the first joining region A1 to a farther distal side. In step S113, an incision is formed as shown in FIG. 24 such that jaws of the linear stapler 130 can be inserted into the first joining region A1 along the first separating line L1 defined by the first groove portion 22a using the first dissecting part 55a of the surgical instrument 1 of the embodiment. Further, when the region to be joined to complete the pouch S2 is sutured as a whole in the above-mentioned step S112, step S113 may not be performed.

After step S114, as shown in FIGS. 25 and 26, the stomach wall is further separated from the incision along the first separating line L1 while being joined using the known linear stapler 130 (an additional joining process, step S115, see FIG. 20). Further, in step S115, the stomach wall may not be separated. In step S115, the case in which the stomach wall is not separated has larger strength in the vicinity of the bypass B2 that the case in which the stomach wall is separated. Necessity of the separation of the stomach wall may be determined in combination with the dimension of the known linear stapler 130 and the length to be joined.

After step S115, the jejunum J1 is separated using the known method as shown in FIG. 27, the anus-side portion of the separation position of the jejunum J1 is inosculated with the pouch S2, and the mouth-side portion of the separation position of the jejunum J1 is inosculated at a wall closer to the anus than the separation position of the jejunum J1 (an alimentary canal reconstruction process, step S116, see FIG. 20). As shown in FIG. 27, a bypass B1 connected from the pouch S2 to the jejunum J1 is formed in step S116.

The bypass B2 configured to connect the pouch S2 and the remaining stomach S3 with no leakage can be formed in substantially the same sequence as the forming sequence of the pouch S2 in the known Roux-en Y gastric bypass through the processes of the above-mentioned steps S111 to S116.

In the gastric bypass of the embodiment, like treatment with the endoscope after the known Roux-en-Y gastric bypass, as the endoscope 90 is guided to the duodenum retrogradely via the jejunum J1 as shown in FIG. 28, treatment or inspection in the vicinity of the duodenal papilla serving as a target, for example, removal of a cholesterol gallstone or the like, can be performed. Further, in the embodiment, as shown in FIG. 29, the endoscope 90 can be guided to the duodenum through the bypass B2.

If the endoscope 90 can be guided to the duodenum through the bypass B2, a path is shorter than that of the case in which the endoscope 90 is guided to the duodenum retrogradely via the jejunum J1, and the endoscope 90 can be easily guided to the vicinity of the duodenal papilla to perform endoscopic retrograde cholangiopancreatography (ERCP) of the vicinity of the duodenal papilla serving as a target.

In addition, a general endoscope for the alimentary canal may not have an insertion section that is elongated enough to arrive at the duodenal papilla along the path that reaches the duodenum retrogradely from the mouth via the jejunum J1 after the known Roux-en-Y gastric bypass. In the above-mentioned endoscope, the distal end of the insertion section arrives at the duodenum while the jejunum J1 is folded to reduce a path, and the procedure is complicated. In the gastric bypass of the embodiment, as the above-mentioned bypass B2 is formed upon formation of the pouch S2, the shortest path from the mouth to the duodenum is a length that is not much different from a preoperative state. As a result, when the procedure using the endoscope 90 is performed at the vicinity of the duodenal papilla serving as a treatment target without limitation to removal of a cholesterol gallstone, in comparison with the conventional procedure via the jejunum J1, the endoscope 90 can easily arrive at the treatment target. In addition, after the gastric bypass of the embodiment, the ERCP using a conventional side view endoscope can be performed, and a treatment property is also improved in comparison with a direct view endoscope used in the ERCP after a Roux-en-Y reconstruction method.

(Variant)

Figure 30:
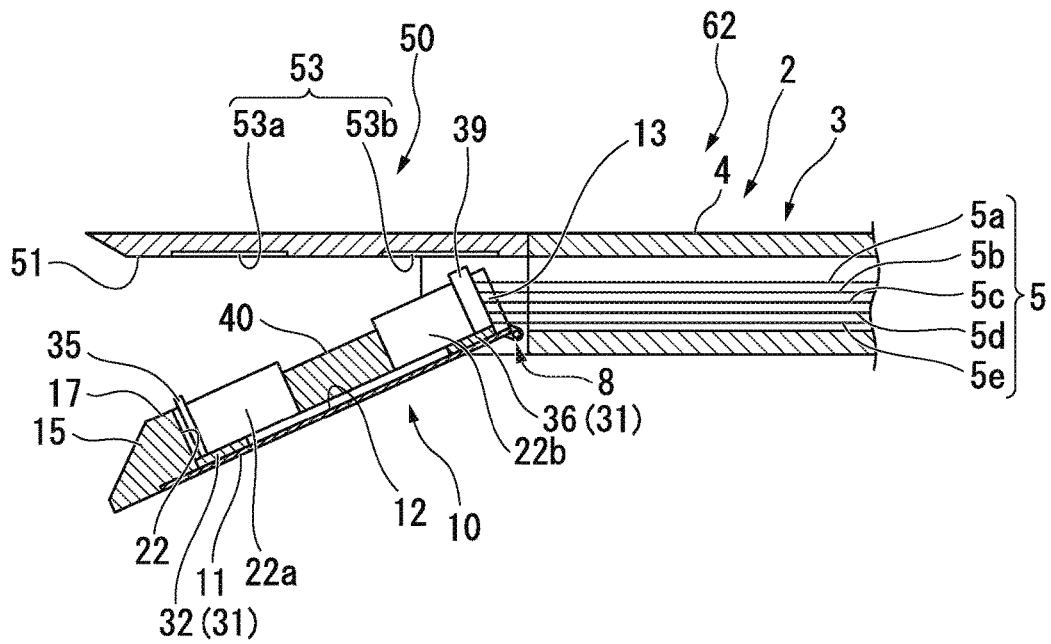
FIG. 30 is a cross-sectional view showing a configuration of a variant of the embodiment.
Figure 31:
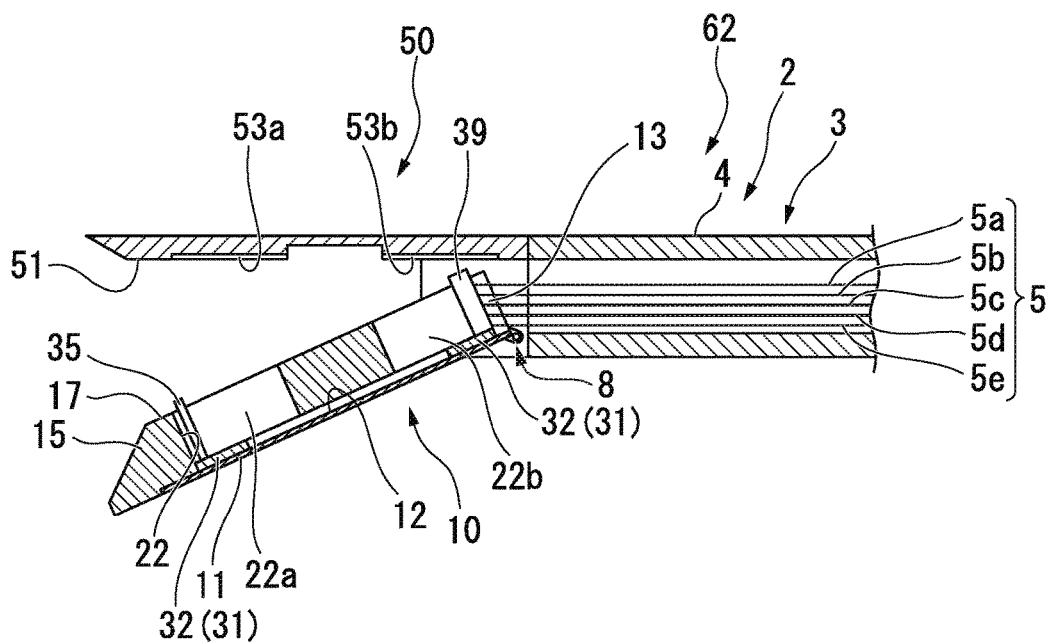
FIG. 31 is a cross-sectional view showing another configuration example of the variant of the embodiment.
Figure 32:
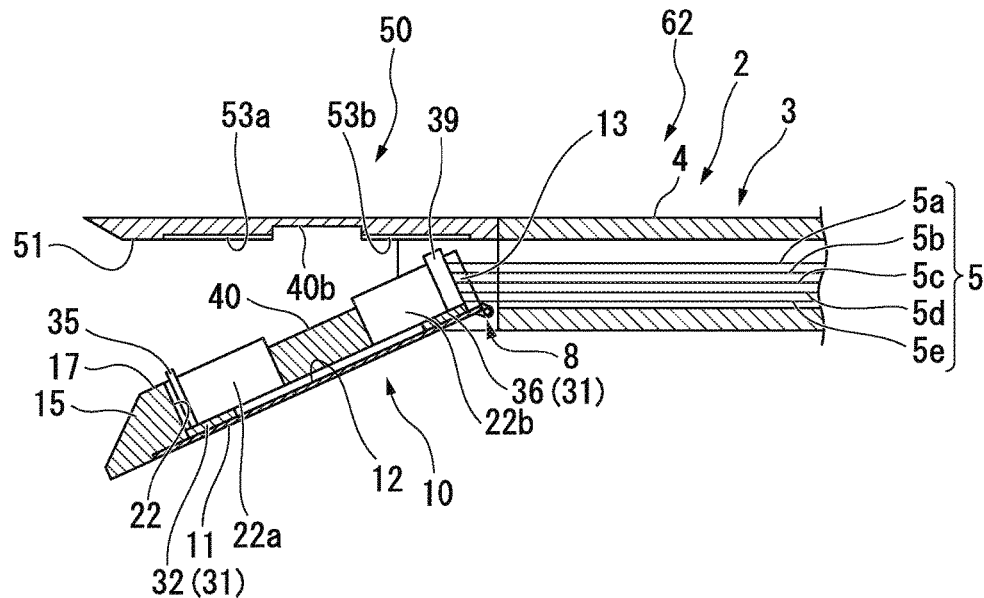
FIG. 32 is a cross-sectional view showing still another configuration example of the variant of the embodiment.

Next, a variant of the first embodiment will be described. FIG. 30 is a cross-sectional view showing a configuration of a variant of the embodiment. FIG. 31 is a cross-sectional view showing another configuration example of the variant of the embodiment. FIG. 32 is a cross-sectional view showing still another configuration example of the variant of the embodiment.

As shown in FIG. 30, in the variant, a recessed portion 40 having a concave shape with respect to the first grasping surface 17 is disposed at the preservation region A3 disposed between the distal end and the proximal end of the first jaw 10.

The recessed portion 40 is set based on a dimension of the tissue serving as a joining and separating target such that the living body tissue is not worn in a process of grasping the living body tissue using the first grasping surface 17 and the second grasping surface 51 and shooting the staples 27.

In the variant, for example, invasion into the alimentary canal T1 in the procedure 1 or the bypass B2 in the procedure 2 is small.

Further, as shown in FIG. 31, the recessed portion 40 is not formed at the first grasping surface 17 of the first jaw 10 but the recessed portion 40b may be formed at the second grasping surface 51 of the second jaw 50. Like the recessed portion 40 of the first jaw 10, the recessed portion 40b of the second jaw 50 is set based on the dimension of the tissue serving as a joining and separating target such that the living body tissue is not worn in a process of grasping the living body tissue using the first grasping surface 17 and the second grasping surface 51 and shooting the staples 27.

In addition, as shown in FIG. 32, the first jaw 10 may have the recessed portion 40 and the second jaw 50 may have the recessed portion 40b.

Second Embodiment

Figure 33:
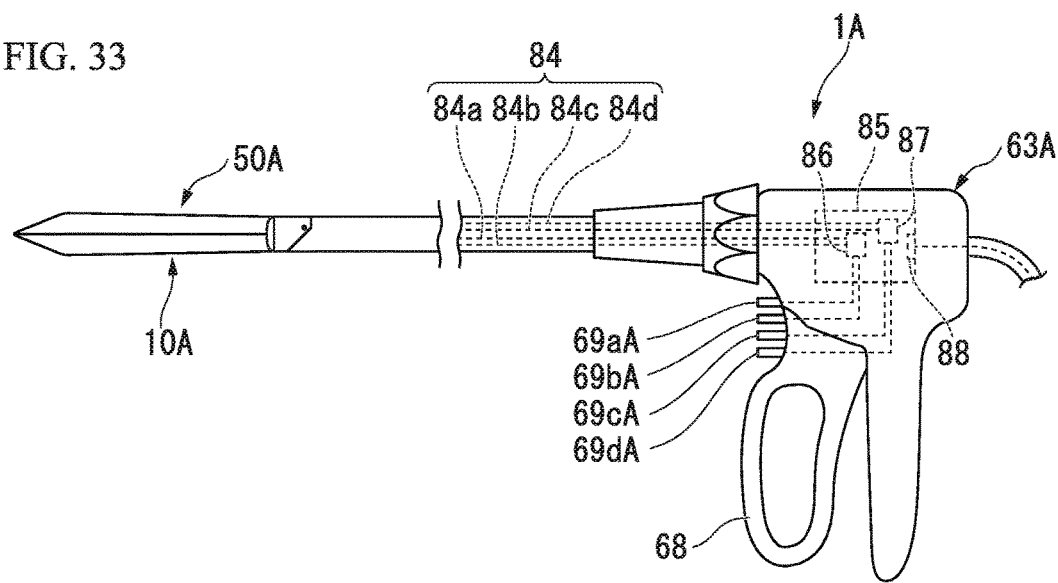
FIG. 33 is a side view showing a surgical instrument of a second embodiment of the present invention.
Figure 34:
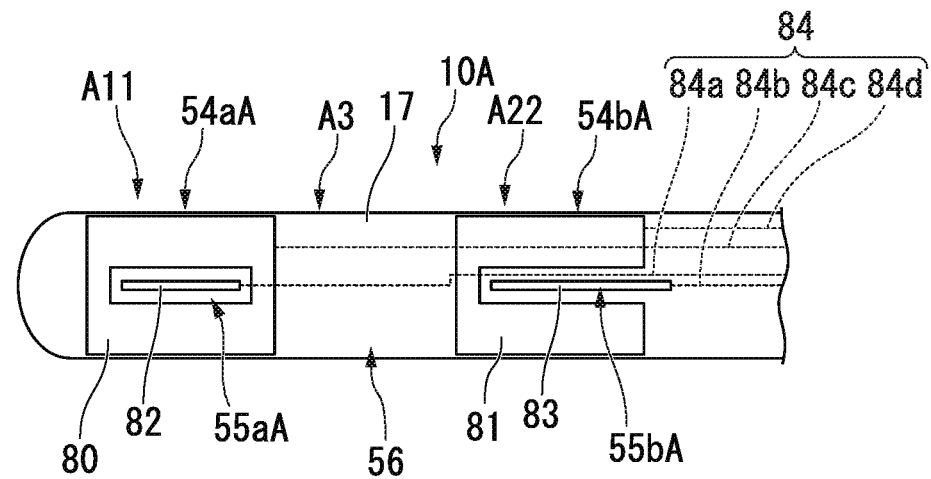
FIG. 34 is a plan view of a first jaw of the surgical instrument.
Figure 35:
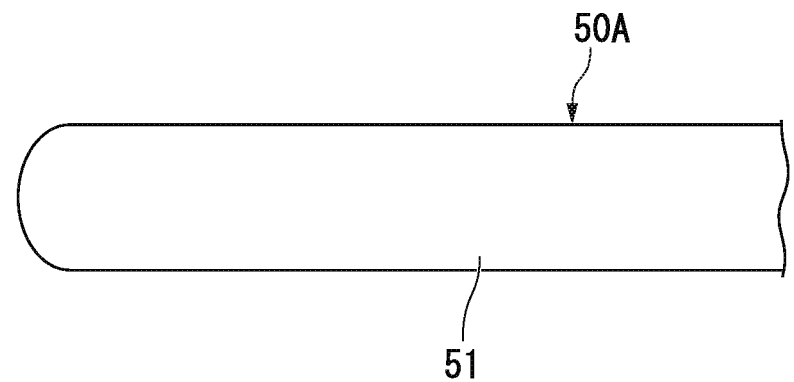
FIG. 35 is a rear view of the first jaw of the surgical instrument.
Figure 36:
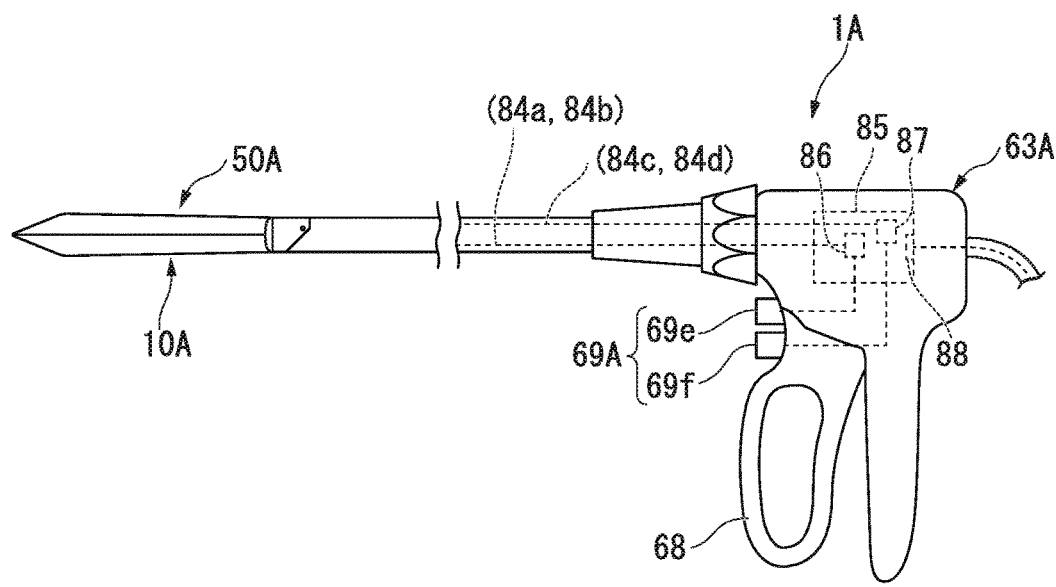
FIG. 36 is a side view showing an example of another configuration of the surgical instrument.
Figure 37:
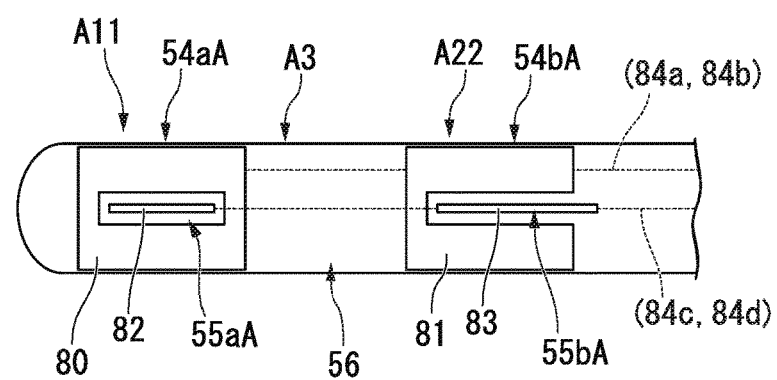
FIG. 37 is a plan view of the first jaw of the surgical instrument shown in FIG. 36.

Next, a second embodiment of the present invention will be described. FIG. 33 is a side view showing a surgical instrument of a second embodiment of the present invention. FIG. 34 is a plan view of a first jaw of the surgical instrument of the embodiment. FIG. 35 is a rear view of the first jaw of the surgical instrument of the embodiment. FIG. 36 is a side view showing an example of another configuration of the surgical instrument of the embodiment. FIG. 37 is a plan view of the first jaw of the surgical instrument shown in FIG. 36.

A surgical instrument 1A of the embodiment shown in FIG. 33 is distinguished from the surgical instrument described in the first embodiment in the following configuration.

First, as shown in FIG. 34, the surgical instrument 1A of the embodiment has a first joining part 54aA configured to apply thermal energy to the living body tissue and join the living body tissue, instead of the first joining part 54a described in the first embodiment.

Further, as shown in FIG. 34, the surgical instrument 1A of the embodiment has a second joining part 54bA configured to apply thermal energy to the living body tissue and join the living body tissue, instead of the second joining part 54b described in the first embodiment.

Further, as shown in FIG. 34, the surgical instrument 1A of the embodiment has a first dissecting part 55aA configured to apply thermal energy to the living body tissue and cut the living body tissue, instead of the first dissecting part 55a described in the first embodiment.

Further, as shown in FIG. 34, the surgical instrument 1A of the embodiment has a second dissecting part 55bA configured to apply thermal energy to the living body tissue and join the living body tissue, instead of the second dissecting part 55b described in the first embodiment.

In the embodiment, the first joining part 54aA, the second joining part 54bA, the first dissecting part 55aA and the second dissecting part 55bA apply thermal energy to the living body tissue using electricity as a whole. When the thermal energy is applied to the living body tissue, in a circumstance in which tension is applied, the living body tissue is heated to about 200° C. to be separated, and when no tension is applied, the temperature is increased to about 300° C. to heat the living body tissue and the living body tissue is separated. In addition, when the living body tissue is thermally denaturated at a predetermined temperature of less than 250° C. the living body tissue can be joined.

The first joining part 54aA and the second joining part 54bA constitutes a thermal bonding mechanism configured to adhesively join a plurality of tissues in a state in which the plurality of tissues separated from each other are grasped by the first jaw 10 and the second jaw 50.

The first joining part 54aA of the embodiment has a first surface heater 80 corresponding to the first suture region A1 in the first embodiment and configured to define a first joining region A11 set to the same region as the first suture region A1, and a temperature sensor (for example, a thermistor), which is not shown, configured to measure a heating temperature by the first surface heater 80.

The second joining part 54bA of the embodiment has a second surface heater 81 corresponding to the second suture region A2 in the first embodiment and configured to define a second joining region A22 set to the same region as the second suture region A2, and a temperature sensor (for example, a thermistor), which is not shown, configured to measure a heating temperature by the second surface heater 81.

The first dissecting part 55aA of the embodiment has a first linear heater 82 corresponding to the first groove portion 22a in the first embodiment, extending in the longitudinal central axis direction of the first jaw 10 and disposed at the first grasping surface 17 of the first jaw 10, and a temperature sensor (for example, a thermistor), which is not shown, configured to measure a heating temperature by the first linear heater 82.

The second dissecting part 55bA of the embodiment has a second linear heater 83 corresponding to the second groove portion 22b in the first embodiment, extending in the longitudinal central axis direction of the first jaw 10 and disposed at the first grasping surface 17 of the first jaw 10, and a temperature sensor (for example, a thermistor), which is not shown, configured to measure a heating temperature by the second linear heater 83.

In addition, in the embodiment, in the connecting member 5 and the transmission member 71 described in the first embodiment, only the first connecting member 5a and the first transmission member 71a (see FIG. 1) are disposed at the surgical instrument 1A. Further, as shown in FIGS. 33 and 34, power lines 84 (a power line 84a, a power line 84b, a power line 84c, and a power line 84d) configured to supply electricity to the first surface heater 80, the second surface heater 81, the first linear heater 82 and the second linear heater 83 according to operation of the operation section 63 extend from the operation section 63 to the cartridge 2. The power lines 84 are connecting members configured to electrically connect the operation section 63A (to be described below) and the first jaw 10 of the embodiment, and transmission members configured to transmit electricity from the operation section 63A to the first jaw 10 of the embodiment.

The power line 84a and the power line 84b are connected to a joining current controller 86 disposed at a temperature adjusting part 85.

The power line 84c and the power line 84d are connected to a separating current controller 87 disposed at the temperature adjusting part 85.

As shown in FIGS. 33 and 35, the second jaw 50A of the embodiment is distinguished from the second jaw 50 disclosed in the first embodiment in that the forming pockets 52 and the clearance groove 53 are not formed but the second jaw 50A is coated with an insulating body as a whole.

Further, in the embodiment, in order to make the cartridge 2 and the stapler 60 attachable and detachable, each of the power line 84a, the power line 84b, the power line 84c and the power line 84d has a contact structure that can be detachably attached to an intermediate portion thereof.

The surgical instrument 1A of the embodiment further has a operation section 63A configured to manipulate the first joining part 54aA, the second joining part 54bA, the first dissecting part 55aA and the second dissecting part 55bA by switching supply states of electricity for the first joining part 54aA, the second joining part 54bA, the first dissecting part 55aA and the second dissecting part 55bA, instead of the operation section 63 described in the first embodiment.

The operation section 63A shown in FIG. 33 has the movable handle 68 for the opening/closing operation described in the first embodiment, a switch part 69A configured to switch on and off the supply states of electricity for the first surface heater 80, the second surface heater 81, the first linear heater 82 and the second linear heater 83, and the temperature adjusting part 85 configured to control a heat generating temperature in the first surface heater 80, the second surface heater 81, the first linear heater 82 and the second linear heater 83.

The switch part 69A has a first joining switch 69aA connected to the first surface heater 80 of the first joining part 54aA via the temperature adjusting part 85, a second joining switch 69bA connected to the second surface heater 81 of the second joining part 54bA via the temperature adjusting part 85, a first separation switch 69cA connected to the first linear heater 82 of the first dissecting part 55aA via the temperature adjusting part 85, and a second separation switch 69dA connected to the second linear heater 83 of the second dissecting part 55bA via the temperature adjusting part 85.

Further, as shown in FIG. 36, the switch part 69A of the operation section 63A may have a joining switch 69e also functions as both of the first joining switch 69aA and the second joining switch 69bA, and a separation switch 69f also functions as both of the first separation switch 69cA and the second separation switch 69dA, instead of the first joining switch 69aA, the second joining switch 69bA, the first separation switch 69cA and the second separation switch 69dA. In this case, since the first joining part 54aA and the second joining part 54bA are not individually driven, the power line 84a and the power line 84b may be provided as a single line for combined use. Similarly, in this case, as shown in FIG. 37, since the first dissecting part 55aA and the second dissecting part 55bA are not individually driven, the power line 84c and the power line 84d may be provided as a single line for combined use.

The temperature adjusting part 85 shown in FIGS. 33 and 36 receives supply of electricity from a power supply means (for example, an external power supply apparatus), which is not shown, and controls power supplied to the first surface heater 80, the second surface heater 81, the first linear heater 82 and the second linear heater 83 according to operation of the switch part 69A. The temperature adjusting part 85 of the embodiment has the joining current controller 86, the separating current controller 87, and a connector section 88 configured to receive supply of power from an external power supply apparatus or the like.

The joining current controller 86 controls the first surface heater 80 and the second surface heater 81 with reference to the temperature sensors according to operation of the first joining switch 69aA or the second joining switch 69bA such that the living body tissue reaches a temperature at which joining through thermal denaturation is possible.

The separating current controller 87 controls the first linear heater 82 and the second linear heater 83 with reference to the temperature sensors according to operation of the first joining switch 69aA or the second joining switch 69bA such that the living body tissue reaches a temperature at which incision by thermal energy is possible. Further, the first linear heater 82 and the second linear heater 83 may be formed of, for example, a nichrome wire.

The surgical instrument 1A of the embodiment is a monopolar type instrument connected to the external power supply apparatus or the like and used with a counter electrode plate (not shown) adhered to a body surface of a patient. Further, the surgical instrument 1A of the embodiment may be a bipolar type instrument having a passive electrode at the second jaw 50A side. Further, as heat or high frequency waves are used, like a conventional grasping type energy device at the first joining region A11, tissue separation and blood vessel sealing can be performed at only the distal end. Accordingly, separation of the tissue, blood vessel sealing and joining of the tissue can be performed by only the surgical instrument 1A of the embodiment without using both of the surgical instrument 1A and the conventional energy device during surgery.

Even in the embodiment, like the first embodiment, one or both of joining and separation can be performed on two places separated to sandwich the preservation region A3 therebetween using the first joining part 54aA, the second joining part 54bA, the first dissecting part 55aA and the second dissecting part 55bA.

In addition, in the embodiment, the heater, the power line, the switch and the temperature control circuit configured to perform joining and separating of the living body tissue are provided, and thus the configuration is simpler and a degree of freedom of disposition of the components is higher than that of the first embodiment.

Further, since the tissue is joined using the thermal energy in the embodiment, falling of the staples 27 shot in a non-sutured state which may be occurred in the surgical instrument 1 described in the first embodiment does not occur in the surgical instrument 1A of the embodiment.

Third Embodiment

Figure 38:
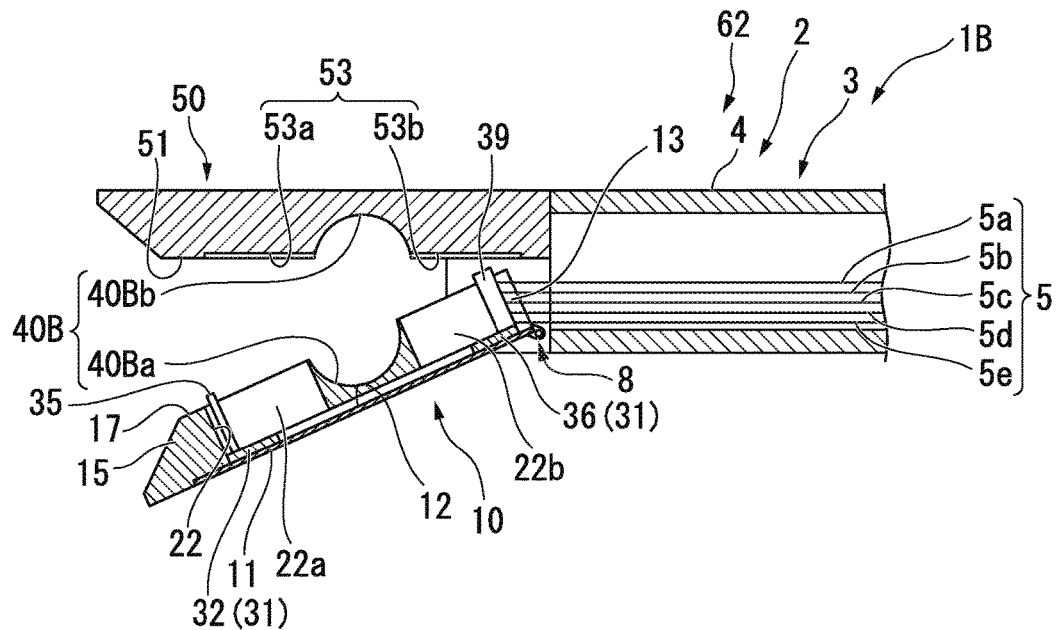
FIG. 38 is a cross-sectional view showing a cartridge in a surgical instrument of a third embodiment of the present invention.

Next, a third embodiment of the present invention will be described. FIG. 38 is a cross-sectional view showing a cartridge in a surgical instrument of the embodiment.

As shown in FIG. 38, a surgical instrument 1B of the embodiment has the recessed portion 40B formed in a concave shape with respect to the first grasping surface 17 and the second grasping surface 51 in the preservation region A3 disposed between the distal end and the proximal end of the first jaw 10.

The recessed portion 40B of the embodiment is different from the recessed portion 40 described in the variant of the first embodiment, and is formed at the first jaw 10 and the second jaw 50 such that the medical instrument different from the surgical instrument 1B of the embodiment can be surrounded by the recessed portion 40B.

The recessed portion 40B has a first recessed portion 40Ba formed at a portion of the first grasping surface 17 of the first jaw 10, and a second recessed portion 40Bb formed at a portion of the second grasping surface 51 of the second jaw 50.

In the embodiment, the first recessed portion 40Ba and the second recessed portion 40Bb have substantially semicylindrical inner surfaces when the first jaw 10 and the second jaw 50 have a cylindrical inner surface in a closed state. Dimensions of the first recessed portion 40Ba and the second recessed portion 40Bb are optimized in consideration of a dimension of a medical instrument used in combination with the surgical instrument 1B of the embodiment and a procedure to which the surgical instrument 1B of the embodiment is applied.

Next, examples of several specific procedures using the surgical instrument 1B of the embodiment are disclosed.

(Procedure 3. Laparoscopic Cardioplasty)

Figure 39:
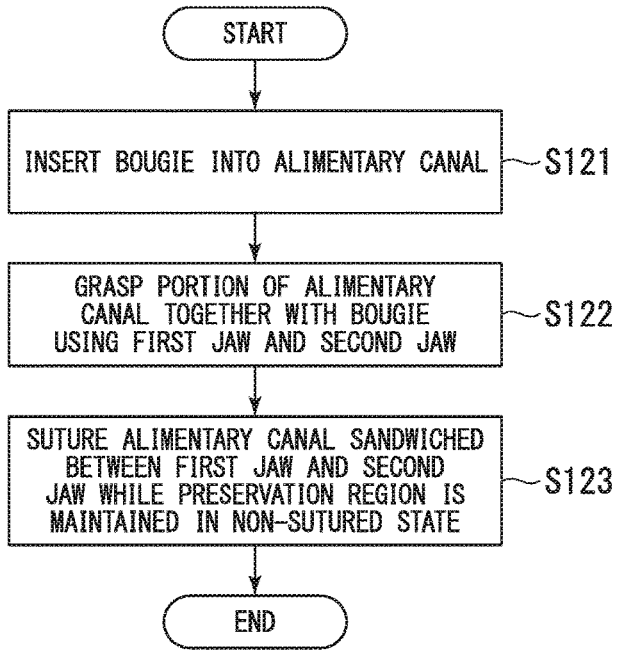
FIG. 39 is a flowchart showing a sequence of laparoscopic cardioplasty using the surgical instrument of the embodiment.
Figure 40:
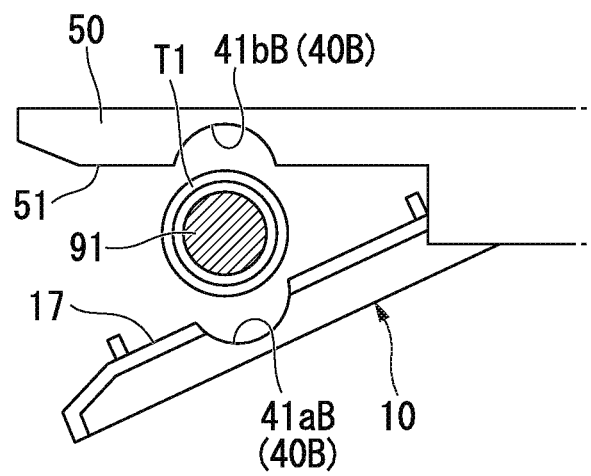
FIG. 40 is a view showing a state in which the surgical instrument approaches the alimentary canal in laparoscopic cardioplasty using the surgical instrument of the embodiment.
Figure 41:
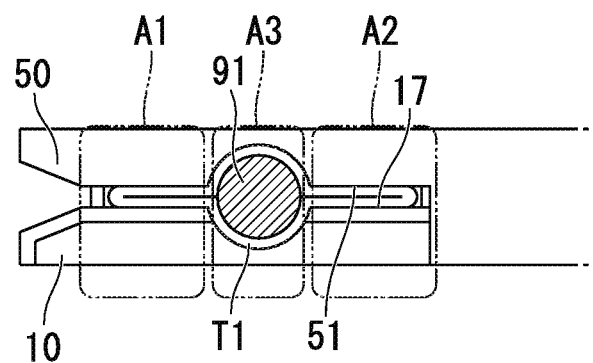
FIG. 41 is a view showing a grasping and joining state of the alimentary canal in laparoscopic cardioplasty using the surgical instrument of the embodiment.

An example of a specific procedure in the case in which two places separated a predetermined interval in the living body tissue are joined using the surgical instrument 1B is disclosed. FIG. 39 is a flowchart showing a sequence of laparoscopic cardioplasty using the surgical instrument of the embodiment. FIG. 40 is a view showing a state in which the surgical instrument approaches the alimentary canal in laparoscopic cardioplasty using the surgical instrument of the embodiment. FIG. 41 is a view showing a grasping and joining state of the alimentary canal in laparoscopic cardioplasty using the surgical instrument of the embodiment.

First, a person who performs laparoscopic cardioplasty attaches a trocar to the abdominal wall through microincision, and guides the surgical instrument 1B of the embodiment into the abdominal cavity through the trocar. Further, the person who performs laparoscopic cardioplasty inserts a bougie 91 that defines an inner diameter upon formation of a cardiac orifice from the mouth to the stomach through the alimentary canal T1 as shown in FIG. 40 (a bougie insertion process, step S121, see FIG. 39).

In the example of the procedure, a dimension of the recessed portion 40B of the surgical instrument 1B is a dimension conforming to a column having an outer diameter obtained by adding a thickness of the alimentary canal tissue to an outer diameter of the bougie 91.

Next, the gastroesophageal joining part or a portion of the alimentary canal T1 in the vicinity of the esophagus is grasped with the bougie 91 as shown in FIG. 41 by the first jaw 10 and the second jaw 50 of the surgical instrument 1B (a grasping process, step S122, see FIG. 39). In the embodiment, the bougie 91 is inserted into the gastroesophageal joining part or the alimentary canal T1 in the vicinity of the esophagus. For this reason, the alimentary canal T1 is grasped with the bougie 91 by the first jaw 10 and the second jaw 50. The bougie 91 supports the alimentary canal T1 from the inside of the alimentary canal T1 to maintain the alimentary canal T1 in a tubular shape. Here, an inner diameter of the alimentary canal T1 does not become smaller than an outer diameter of the bougie 91. In addition, when the portion of the alimentary canal T1 is grasped by the first jaw 10 and the second jaw 50 in a state in which the bougie 91 is in the alimentary canal T1, the bougie 91 should enter the recessed portion 40B in order to appropriately close the first jaw 10 and the second jaw 50. When the first jaw 10 and the second jaw 50 are closed in a state in which the bougie 91 enters the recessed portion 40B, the alimentary canal T1 is deformed to have an inner diameter defined by the outer diameter of the bougie 91, and a portion of the alimentary canal tissue which become redundant due to the deformation is disposed at one or both of the first suture region A1 and the second suture region A2 of the surgical instrument 1B.

In addition, the bougie 91 has a rod shape extending in the alimentary canal T1 in a direction substantially along a centerline of the alimentary canal T1. For this reason, when the bougie 91 enters the recessed portion 40B to close the first jaw 10 and the second jaw 50, the longitudinal central axis of the first jaw 10 is directed as the bougie 91 is guided in a direction substantially perpendicular to the centerline of the alimentary canal T1.

Further, in the embodiment, since the recessed portion 40B defines the preservation region A3 in the surgical instrument 1B, when the bougie 91 enters the recessed portion 40B to close the first jaw 10 and the second jaw 50, the preservation region A3 is disposed at a substantially intermediate portion in the radial direction of the alimentary canal T1.

In a state in which the alimentary canal T1 is appropriately grasped by the first jaw 10 and the second jaw 50, the alimentary canal T1 is grasped by the first jaw 10 and the second jaw 50 while the alimentary canal T1 is included in both of the first joining region A1 and the second joining region A2.

When the alimentary canal T1 is appropriately grasped by the first jaw 10 and the second jaw 50 in this way, the first joining operation handle 69a and the second joining operation handle 69b are manipulated, and the first separation operation handle 69c and the second separation operation handle 69d are not manipulated (a simultaneous suture process, step S123, see FIG. 39). In step S123, the staples 27 are shot from the housing portion 18 in the first joining part 54a and the second joining part 54b according to operation of the first joining operation handle 69a and the second joining operation handle 69b. Some of the staples 27 shot from the housing portion 18 suture the alimentary canal T1 in a state in which the alimentary canal T1 is folded.

In the laparoscopic cardioplasty using the surgical instrument 1B, a function of a lumen of the alimentary canal T1 is maintained at a portion defined by an inner diameter of the preservation region A3 defined by the recessed portion 40B of the first jaw 10 with respect to the alimentary canal T1, and the other portion is joined. As a result, the alimentary canal T1 is formed to have a diameter reduced to be smaller than the diameter before suture.

In the laparoscopic cardioplasty using the surgical instrument 1B, since a size of the portion functioning as the lumen after suture is uniquely determined by the dimension of the recessed portion 40B serving as the preservation region A3 of the first jaw 10, the cardiac orifice can be easily formed without necessity of adjusting the diameter of the alimentary canal T1 by performing the suture a plurality of times from a plurality of directions outside the alimentary canal T1.

Further, in the laparoscopic cardioplasty using the surgical instrument 1B, since a region remaining as the lumen after joining has a tubular shape having an inner diameter corresponding to an outer diameter of the bougie 91, if the outer diameter of the bougie 91 is appropriately selected, the cardiac orifice can be easily formed in a short time and adjustment of the inner diameter of the alimentary canal T1 after joining does not need to be considered during the joining.

Further, in the laparoscopic cardioplasty using the surgical instrument 1B, two places separated to sandwich the centerline of the alimentary canal T1 therebetween are sutured by one suture operation. For this reason, the two separated places can be sutured using the surgical instrument 1B from the direction in which the surgical instrument 1B can most easily approach the alimentary canal T1.

Further, in the laparoscopic cardioplasty using the surgical instrument 1B, since the first suture region A1 and the second suture region A2 can be sutured while the alimentary canal T1 is grasped by the first jaw 10 and the second jaw 50, in comparison with the case in which the flexible tissue of the alimentary canal is grasped and sutured a plurality of times, precise suture can be easily performed.

Further, the above-mentioned procedure can be applied to a procedure of joining or separating both ends while preserving the luminal tissue in the lumen state between the two areas with respect to the two separated areas in the living body tissue, in addition to the laparoscopic cardioplasty. For example, the surgical instrument 1B of the embodiment can be used in the procedure of joining or separating the living body tissue around the blood vessel or the urinary duct without damage.

(Procedure 4. Laparoscopic Roux-En Y Gastric Bypass)

A specific example in the case in which the bypass B2 that can be used to pass through the endoscope 90 to the duodenum after reconstruction is formed at the stomach S1 using the surgical instrument 1B in the process of forming the pouch S2 in the stomach S1 of a patient who receives the Roux-en Y gastric bypass is shown.

Figure 42:
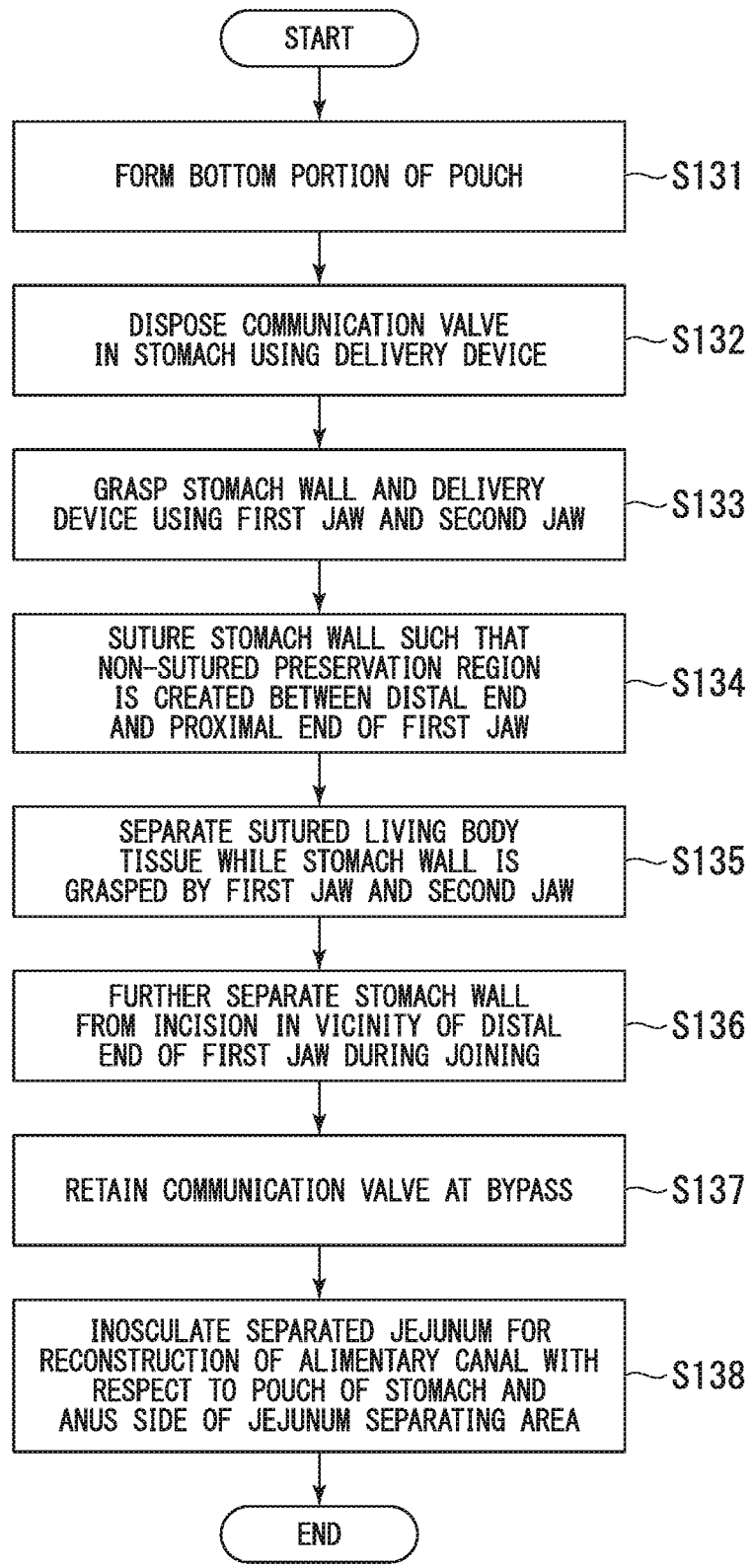
FIG. 42 is a flowchart showing a sequence of a laparoscopic Roux-en Y gastric bypass using the surgical instrument of the embodiment.
Figure 43:
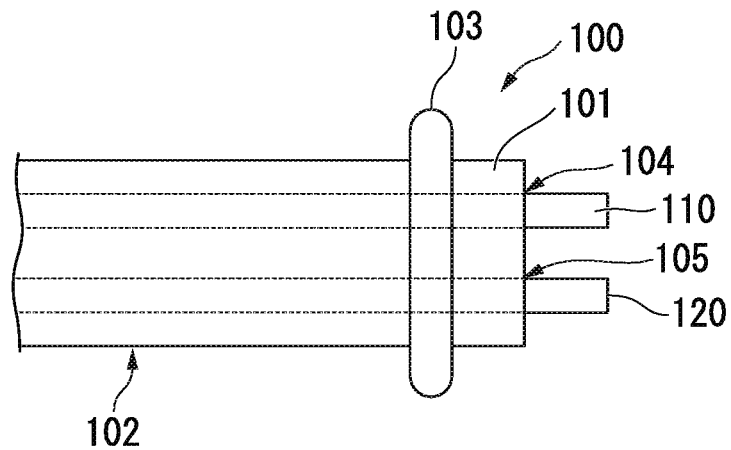
FIG. 43 is a side view showing a portion of a delivery device used for a laparoscopic Roux-en Y gastric bypass together with the surgical instrument of the embodiment.
Figure 44:
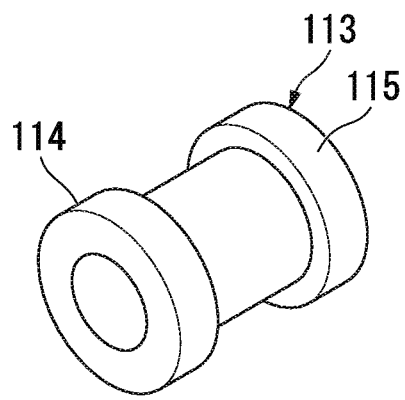
FIG. 44 is a perspective view showing a communication valve retained in the stomach by the delivery device.
Figure 45:
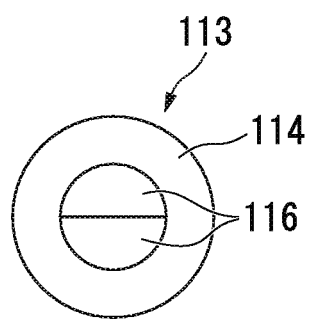
FIG. 45 is a front view showing the communication valve.
Figure 46:
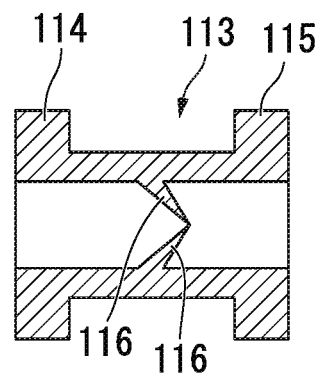
FIG. 46 is a cross-sectional view in an axial direction of the communication valve.
Figure 47:
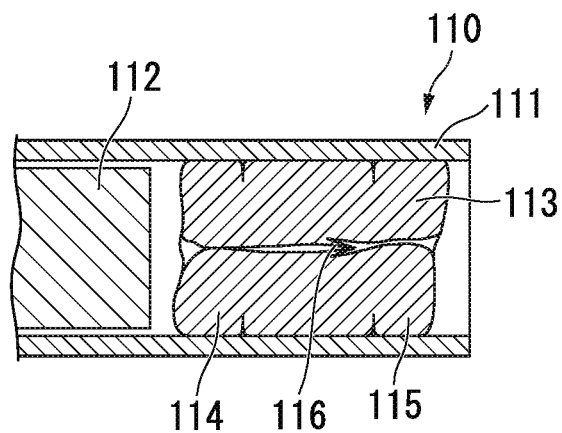
FIG. 47 is a cross-sectional view showing a portion of a communication valve retainer attached to the delivery device.
Figure 48:
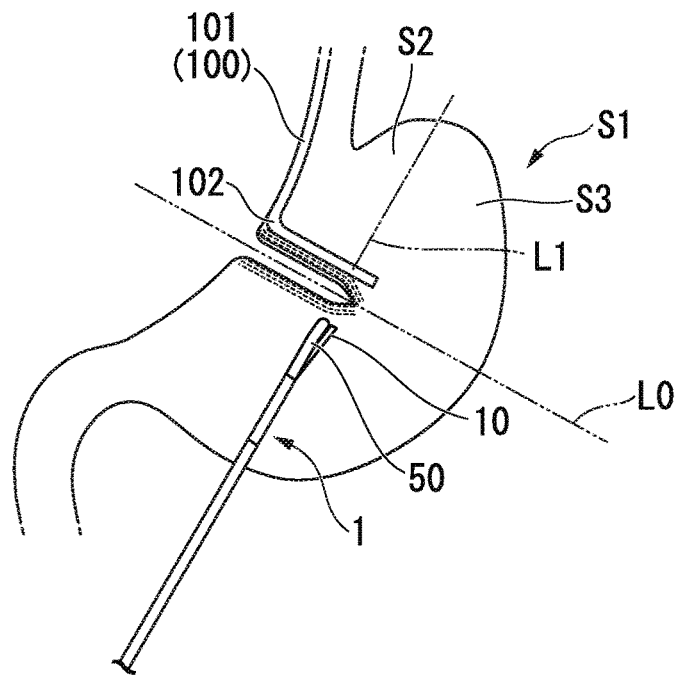
FIG. 48 is a schematic view showing an introduction state of the delivery device in a laparoscopic Roux-en Y gastric bypass using the surgical instrument of the embodiment.
Figure 49:
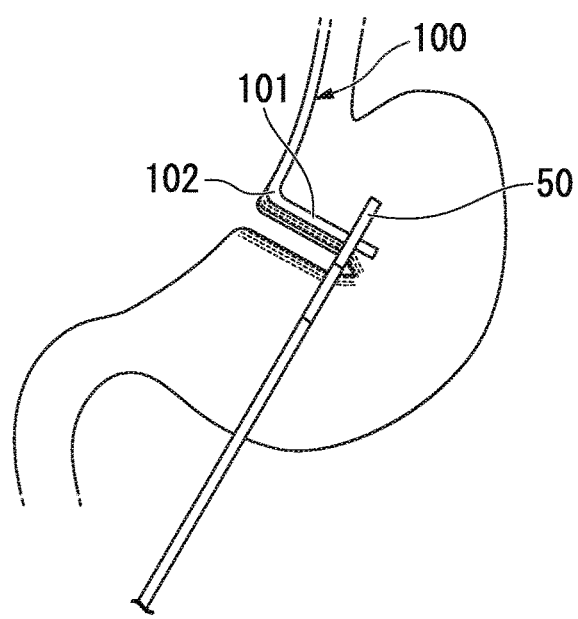
FIG. 49 is a schematic view showing a process of forming a bypass in a laparoscopic Roux-en Y gastric bypass using the surgical instrument of the embodiment.
Figure 50:
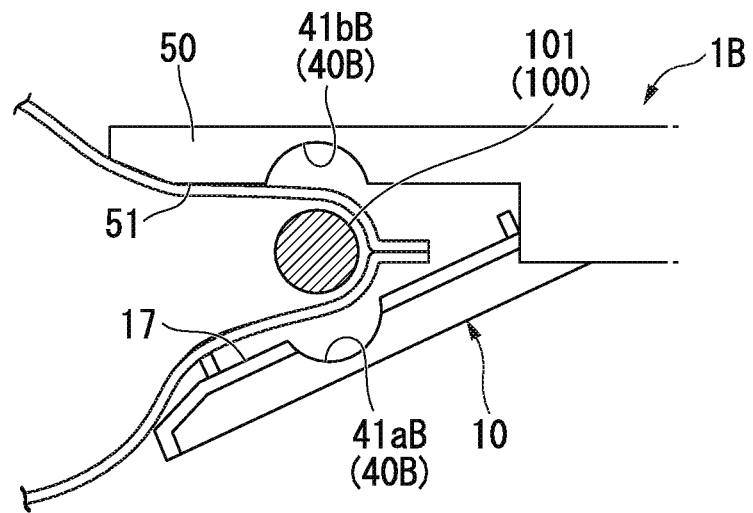
FIG. 50 is a schematic view showing a state of approaching the stomach wall for forming the bypass in a laparoscopic Roux-en Y gastric bypass using the surgical instrument of the embodiment.
Figure 51:
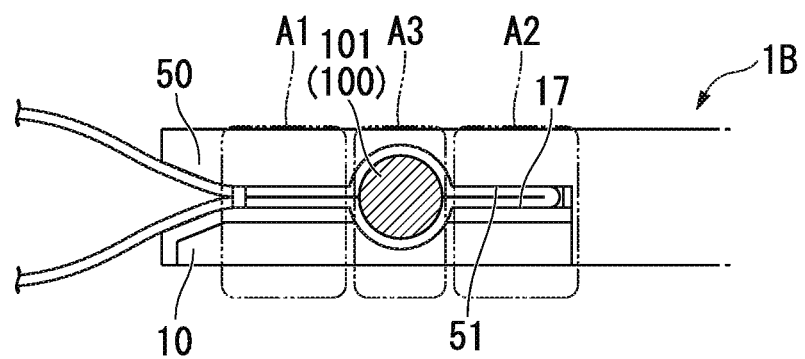
FIG. 51 is a schematic view showing a joining and separating state of the stomach wall together with grasping of the stomach wall for forming the bypass in a laparoscopic Roux-en Y gastric bypass using the surgical instrument of the embodiment.
Figure 52:
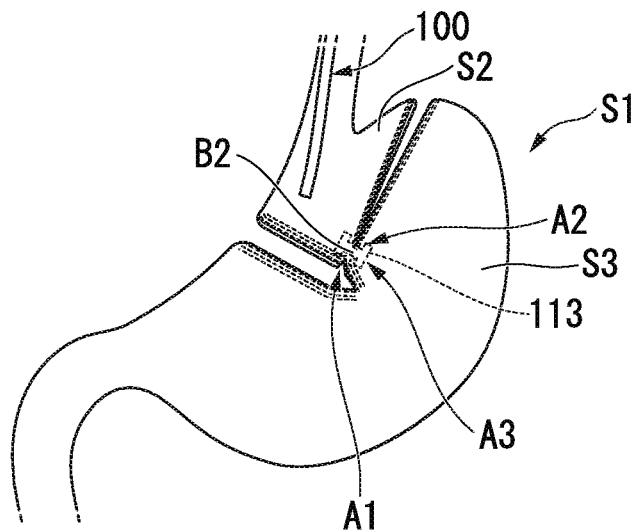
FIG. 52 is a schematic view showing a state in which a communication valve is retained in the bypass in a laparoscopic Roux-en Y gastric bypass using the surgical instrument of the embodiment.
Figure 53:
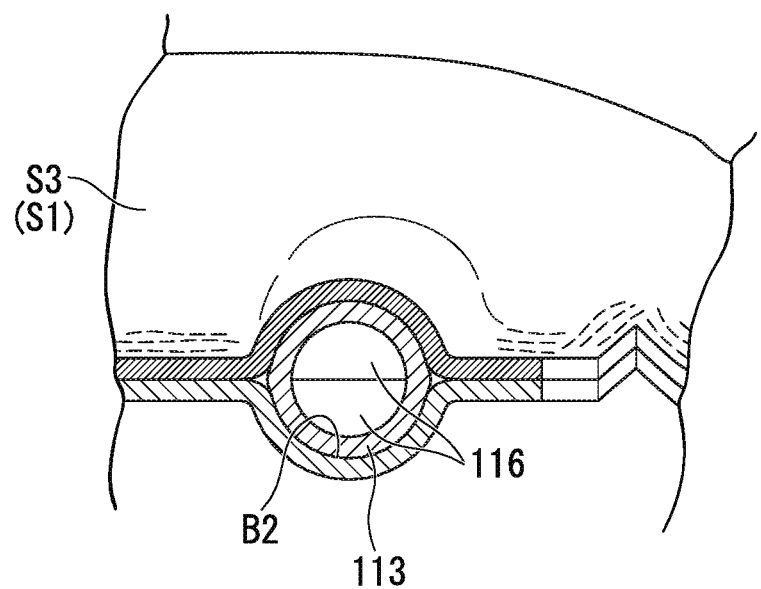
FIG. 53 is a schematic view showing a state in which the communication valve is retained in the bypass in a laparoscopic Roux-en Y gastric bypass using the surgical instrument of the embodiment.

FIG. 42 is a flowchart showing a sequence of laparoscopic Roux-en Y gastric bypass using the surgical instrument of the embodiment. FIG. 43 is a side view showing a portion of a delivery device used for a laparoscopic Roux-en Y gastric bypass together with the surgical instrument of the embodiment. FIG. 44 is a perspective view showing a communication valve retained in the stomach by the delivery device. FIG. 45 is a front view showing the communication valve. FIG. 46 is a cross-sectional view in an axial direction of the communication valve. FIG. 47 is a cross-sectional view showing a portion of a communication valve retainer attached to the delivery device. FIG. 48 is a schematic view showing an introduction state of the delivery device in a laparoscopic Roux-en Y gastric bypass using the surgical instrument of the embodiment. FIG. 49 is a schematic view showing a process of forming a bypass in a laparoscopic Roux-en Y gastric bypass using the surgical instrument of the embodiment. FIG. 50 is a schematic view showing a state of approaching the stomach wall for forming the bypass in a laparoscopic Roux-en Y gastric bypass using the surgical instrument of the embodiment. FIG. 51 is a schematic view showing a joining and separating state of the stomach wall together with grasping of the stomach wall for forming the bypass in a laparoscopic Roux-en Y gastric bypass using the surgical instrument of the embodiment. FIG. 52 is a schematic view showing a retaining state of a communication valve to the bypass in a laparoscopic Roux-en Y gastric bypass using the surgical instrument of the embodiment. FIG. 53 is a schematic view showing a retaining state of the communication valve in the bypass in a laparoscopic Roux-en Y gastric bypass using the surgical instrument of the embodiment.

First, the trocar is attached to the abdominal wall through microincision, and the medical instruments are introduced into the abdominal cavity via the trocar.

In the process of forming the pouch S2 in the stomach S1, the known linear stapler 130 is guided into abdominal cavity via the trocar firstly, and the linear stapler 130 is used.

Next, the bottom section of the pouch S2 is prepared using the linear stapler 130 as in the conventional method (see FIGS. 21 and 22) (a first joining/separating process, step S131, see FIG. 42).

After step S131, before formation of the bypass B2 described in the first embodiment, a delivery device 100 configured to deliver a communication valve 113 that brings the pouch S2 and the remaining stomach S3 in communication with each other into the stomach S1 is inserted from the mouth to the stomach S1 (a communication valve introduction process, step S132, see FIG. 42).

As shown in FIG. 43, the delivery device 100 used in the embodiment has an insertion body 101 that is able to be inserted into a body, an active bending portion 102 disposed at a position separated at the proximal side by a predetermined length from the distal end of the insertion body 101 to change a direction of the distal end of the insertion body 101, an expandable balloon 103 disposed closer to an outer circumferential surface of the insertion body 101 at the distal side than the active bending portion 102, a delivery channel 104 and a channel 105 for an observation means disposed in the insertion body 101, a communication valve retainer 110 disposed in the delivery channel 104 to advance and retreat, and an imaging device 120 disposed in the channel 105 for an observation means to advance and retreat.

The communication valve 113 delivered into the stomach S1 by the delivery device 100 is a valve that is able to be attached to the bypass B2 configured to connect the pouch S2 and the remaining stomach S3 as shown in FIG. 52. As shown in FIGS. 44 to 47, the communication valve 113 is disposed in a sheath 111 of the communication valve retainer 110 in a folded state, and is formed of an elastic member that can be recovered in a predetermined retaining shape when the communication valve 113 is pressed by a pusher 112 to exit through the distal end of the sheath 111.

As shown in FIG. 46, the communication valve 113 has a substantially tubular shape. Openings of both ends of the communication valve 113 have a first flange section 114 and a second flange section 115 having sizes larger than the outer diameter of the intermediate portion of the communication valve 113. The first flange section 114 and the second flange section 115 have outer diameters larger than the outer diameter of the insertion body 101 of the delivery device 100 when recovered to a predetermined retaining shape.

As shown in FIGS. 45 and 46, the communication valve 113 has lips 116 that are opened and closed such that movement of materials from the pouch S2 into the remaining stomach S3 is always restricted and insertion of the endoscope 90 from the pouch S2 into the remaining stomach S3 is possible. For example, a duck bill valve may be employed as the communication valve 113 of the embodiment. In the embodiment, when the communication valve 113 is retained in the bypass B2 such that the first flange section 114 is disposed at the pouch S2 side and the second flange section 115 is disposed at the remaining stomach S3 side, movement of materials from the pouch S2 into the remaining stomach S3 is always restricted, and the lips 116 are pushed to be widened to allow passage of the endoscope upon insertion of the endoscope.

In step S132, as shown in FIG. 48, the delivery device 100 is bent to be disposed in the stomach S1 such that the delivery device 100 is disposed adjacent to the separating line L0 in step S131.

After step S132, as shown in FIGS. 48 and 49, the first jaw 10 and the second jaw 50 of the surgical instrument 1B of the embodiment are guided from the distal end of the separating line L0 in step S131 to be directed in a direction substantially perpendicular to the separating line L0 in step S111, the proximal end of the first jaw 10 is disposed in the vicinity of the distal end of the separating line L0 in step S131, and the stomach S1 is grasped by the first jaw 10 and the second jaw 50 (a grasping process, step S133, see FIG. 42). In a state in which the stomach S1 is grasped by the first jaw 10 and the second jaw 50 in step S133, as shown in FIGS. 50 and 51, the stomach wall is pinched between the first grasping surface 17 and the second grasping surface 51 while inner walls of the stomach S1 come in contact with each other. Further, in the embodiment, the first jaw 10 and the second jaw 50 pinch the stomach wall together with the delivery device 100 such that the recessed portion 40B surrounds an outer circumference of the vicinity of the distal end of the insertion body 101 of the delivery device 100.

After step S133, as shown in FIGS. 51 and 52, the stomach wall is joined at a portion in the vicinity of the proximal end of the first jaw 10 and a portion in the vicinity of the distal end of the first jaw 10 such that the non-sutured preservation region A3 is created between the distal end and the proximal end of the first jaw 10 (a joining process, step S134, see FIG. 42). In the procedure using the surgical instrument 1B of the embodiment in step S134, the staples 27 are shot from the housing portion 18 at both of the first suture region A1 and the second suture region A2 in the surgical instrument 1B, and the suture by the staples 27 is not performed at the recessed portion 40B. A boundary between the recessed portion 40B and the first suture region A1 is sutured by the staples 27 such that there is no leakage. A boundary between the recessed portion 40B and the second suture region A2 is sutured by the staples 27 such that there is no leakage.

A predetermined non-sutured portion defined by a shape of the recessed portion 40B has a luminal shape that connects the pouch S2 and the remaining stomach S3 by the first suture region A1 and the second suture region A2. The lumen-shaped portion functions as the bypass B2 joined by the staples 27 to prevent leakage of the gastric fluid or food to the outside of the stomach and configured to connect the pouch S2 and the remaining stomach S3. An inner diameter of the bypass B2 of the embodiment is substantially equal to the outer diameter of the intermediate portion of the communication valve 113 due to the outer circumferential surface of the insertion body 101 of the delivery device 100, and has a size such that the first flange section 114 and the second flange section 115 are hooked by peripheral tissue of both end openings of the bypass B2.

After step S134, the joined living body tissue is separated while the stomach wall is grasped by the first jaw 10 and the second jaw 50 (a separation process, step S135, see FIG. 42). In step S135, like the first embodiment (see FIGS. 24 and 25), an incision is formed in the first joining region A1 such that jaws of the linear stapler 130 can be inserted along the first separating line L1 defined by the first groove portion 22a. Further, when the region to be joined to complete the pouch S2 is sutured in the above-mentioned step S112 as a whole, step S134 may not be performed.

After step S135, the stomach wall can be further separated from the incision along the first separating line L1 using the known linear stapler 130 during joining (an additional joining process, step S136, see FIG. 42). In step S136, the stomach wall may not be separated. While the stomach wall is not separated in step S136, strength in the vicinity of the bypass B2 is high.

After step S136, the communication valve 113 is retained in the bypass B2 (a valve retaining process, step S137, see FIG. 42). In step S137, the communication valve 113 is pushed into the stomach S1 from the sheath 111 of the communication valve retainer 110 of the delivery device 100 using the pusher 112, a portion of the communication valve 113 is first hooked at the remaining stomach S3 side, a portion of the communication valve 113 is then hooked at the pouch S2 side, and then the delivery device 100 is removed to the outside of the body (see FIGS. 52 and 53).

Further, the retaining of the communication valve 113 in step S137 may be performed before additional joining and separating from the first separating line L1 in step S136.

After step S137, the jejunum J1 is separated through a known method, the anus-side portion of the separation position of the jejunum J1 is inosculated with the pouch S2, and the mouth-side portion of the separation position of the jejunum J1 is inosculated at a wall closer to the anus side than the separation position of the jejunum J1 (an alimentary canal reconstruction process, step S138, see FIGS. 42 and 27).

In substantially the same sequence as the forming sequence of the pouch S2 in the known Roux-en Y gastric bypass by the processes of steps S131 to S138, the bypass B2 configured to connect the pouch S2 and the remaining stomach S3 with no leakage can be formed.

Further, in the embodiment, since the insertion body 101 of the delivery device 100 defines the shape of the bypass B2, as the communication valve 113 that can be engaged to the remaining stomach S3 side and the pouch S2 side to correspond to the outer diameter of the insertion body 101 of the delivery device 100, a structure having a small leakage from the pouch S2 to the remaining stomach S3 can be easily formed.

Further, in the embodiment, since the insertion body 101 of the delivery device 100 defines the shape of the bypass B2 and the shape of the bypass B2 is a tubular shape that conforms to the shape of the outer circumferential surface of the insertion body 101 of the delivery device 100, the bypass B2 can be easily and precisely formed.

As the bypass B2 is formed upon formation of the pouch S2, the endoscope 90 can easily arrive at the remaining stomach S3 or the duodenum when the procedure is performed on the remaining stomach S3 or the duodenum serving as a target using the endoscope 90 via the communication valve 113 without being limited to removal of a cholesterol gallstone. In addition, since the communication valve 113 can restrict movement of food from the pouch S2 into the remaining stomach S3, movement and absorption of the food from the pouch S2 into the remaining stomach S3 can be prevented.

While embodiments of the present invention have been described above in detail with reference to the accompanying drawings, specific configurations are not limited to the embodiments but design changes or the like may be made without departing from the spirit of the present invention.

For example, the operation section configured to perform the joining and separation through a single operation like the suture/separation simultaneous operation section described in the variant of the second embodiment can be applied to the surgical instrument described in the first embodiment. For example, by connecting and linking wires configured to operate the first joining part, the second joining part, the first dissecting part and the second dissecting part, the suture/separation simultaneous operation section configured to perform the suture and separation of the tissue through a single operation can be provided.

In addition, even when the first joining operation handle 69a, the second joining operation handle 69b, the first separation operation handle 69c and the second separation operation handle 69d disclosed in the first embodiment are connected to each other, the suture/separation simultaneous operation section configured to perform the suture and separation of the tissue through a single operation is obtained.

In addition, the components disclosed in the embodiments and the variants may be appropriately combined.

For example, when the first embodiment and the second embodiment are combined, there is provided the surgical instrument in which the first joining part 54aA and the first dissecting part 55aA of the second embodiment using thermal energy are applied to the vicinity of the distal end portions in the pair of grasping parts (for example, the first jaw 10 and the second jaw 50) and the second joining part and the second dissecting part of the first embodiment using a staple and dissecting knife are applied to the vicinity of the proximal end portions in the pair of grasping parts. In this way, the first joining part 54a, the second joining part 54b, the first dissecting part 55a and the second dissecting part 55b described in the first embodiment and the first joining part 54aA, the second joining part 54bA, the first dissecting part 55aA and the second dissecting part 55bA described in the second embodiment may be appropriately selected and applied to the vicinity of the distal end portions and the vicinity of the proximal end portions of the pair of grasping parts.

Further, design changes to the specific configurations are not limited to the above-mentioned matters.

Other aspects of the present invention will be exemplified below.

(Supplementary Statement 1)
Another aspect of the present invention is a joining method of joining living body tissue, the method comprising:
a grasping process of grasping a joining target tissue using a pair of jaws that are able to join the living body tissue; and
a simultaneous joining process of maintaining a non-joined preservation region between the first joining region and the second joining region after the grasping process, and joining the first joining region and the second joining region in a state in which a first joining region of a distal end side and a second joining region of a proximal end side in a longitudinal central axis direction of the pair of jaws grasp the living body tissue.

Further, the simultaneous joining process disclosed in Supplementary Statement 1 may be suture using staples or suture threads, or joining through thermal denaturation of living body tissue by thermal energy.

(Supplementary Statement 2)
In the joining method of the aspect disclosed in Supplementary Statement 1, in the grasping process, two separated tissues are pinched between the pair of jaws, and
in the simultaneous joining process, the two tissues are joined to form a lumen-shaped bypass at the preservation region such that the two tissues are integrated at both of the first joining region and the second joining region.

(Supplementary Statement 3)
In the joining method of the aspect disclosed in Supplementary Statement 2, in the grasping process, a predetermined medical instrument is disposed between the two tissues and the two tissues are grasped together with the medical instrument by the pair of jaws, and
in the simultaneous joining process, the bypass is formed to have a lumen shape to surround the medical instrument in a state in which the medical instrument is disposed in the preservation region.

(Supplementary Statement 4)
In the joining method of the aspect disclosed in Supplementary Statement 3, the medical instrument is a delivery device configured to retain a tube or a valve at the bypass.

(Supplementary Statement 5)
In the joining method of the aspect disclosed in Supplementary Statement 2, in the simultaneous joining process, before the pair of jaws are opened after the joining in the first joining region begins, an incision into which a medical instrument is inserted is formed in the first joining region by separating the living body tissue in the first joining region.

(Supplementary Statement 6)
In the joining method of the aspect disclosed in Supplementary Statement 5, the medical instrument is a joining instrument configured to join the living body tissue in a predetermined linear shape or a joining/separating instrument configured to join the living body tissue in a predetermined linear shape and cut the living body tissue in the linear shape.

(Supplementary Statement 7)
In the joining method of the aspect disclosed in Supplementary Statement 5, in the simultaneous joining process, before the pair of jaws are opened after the joining in the second joining region begins, the living body tissue is separated in the second joining region.

(Supplementary Statement 8)
Another aspect of the present invention is a gastric bypass including forming a bypass configured to bring a pouch formed at the stomach and a remaining stomach separated from the pouch in communication with each other.

(Supplementary Statement 9)

In the gastric bypass of the aspect disclosed in Supplementary Statement 8, the bypass is formed by maintaining a non-joined and non-separated preservation region on a separating line to form the pouch.

(Supplementary Statement 10)

In the gastric bypass of the aspect disclosed in Supplementary Statement 9, the neighboring stomach walls that sandwich a prearranged area serving as the preservation region on the separating line are grasped in a crushed state such that inner surfaces of the stomach come in contact with each other, and two neighboring places that sandwich a prearranged area serving as the preservation region therebetween are simultaneously operated or continuously joined through a single operation.

(Supplementary Statement 11)

In the gastric bypass of the aspect disclosed in Supplementary Statement 8, an opening/closing valve configured to restrict entry of materials from the pouch into the remaining stomach is retained at the bypass.

(Supplementary Statement 12)

In the gastric bypass of the aspect disclosed in Supplementary Statement 11, a delivery device configured to deliver the valve from the mouth to the stomach is inserted into the stomach before formation of the pouch in a state in which the valve is attached, the delivery device is disposed in the stomach to cross a separating line to form the pouch and a portion of the valve is disposed at the remaining stomach side, the bypass is formed as a lumen having a shape that conforms to an exterior of the delivery device using a crossing portion between the delivery device and the separating line as a non-joined and non-separated portion by joining and separating the stomach along the separating line, and when the valve is separated from the delivery device while the delivery device is moved toward the pouch through the bypass, the valve is retained at the bypass to be opened at both of the pouch and the remaining stomach.

While preferred embodiments of the present invention have been described, the present invention is not limited to the embodiments. Additions, omissions, substitutions, and other variations may be made to the present invention without departing from the spirit and scope of the present invention. The present invention is not limited by the above description, but by the appended claims.

What is claimed is:

1. A surgical instrument comprising:
   a pair of grasping parts having distal end portions and proximal end portions, having shapes extending along a longitudinal central axis connecting the distal end portions and the proximal end portions, and having a pair of grasping surfaces disposed to face each other such that the pair of grasping surfaces are capable of grasping living body tissue;
   a first joining part disposed at the vicinity of the distal end portion of the grasping part and configured to irreversibly join the living body tissue grasped by the pair of grasping parts;
   a first dissecting part configured to cut the living body tissue joined by the first joining part in the longitudinal central axis direction in a region in which the living body tissue is joined by the first joining part;
   a second joining part disposed away from the first joining part, disposed at the vicinity of the proximal end portion of the grasping part, and configured to irreversibly join the living body tissue grasped by the pair of grasping parts;
   a second dissecting part configured to cut the living body tissue joined by the second joining part in the longitudinal central axis direction in a region in which the living body tissue is joined by the second joining part; and
   a tissue preservation part disposed between the first joining part and the second joining part, having a recessed portion formed to be recessed with respect to the pair of grasping surface and disposed at the pair of grasping surfaces such that the tissue preservation part is configured to preserve a non-joining region between the first joining part and the second joining part when the first joining part and the second joining part join the living body tissue.

2. The surgical instrument according to claim 1, wherein at least one of the first joining part and the second joining part has a thermal bonding mechanism configured to apply thermal energy by electricity to the living body tissue and adhesively join a plurality of tissues in a state in which the plurality of tissues separated from each other are grasped by the pair of grasping parts.

3. The surgical instrument according to claim 1, wherein at least one of the first joining part and the second joining part has a stapling mechanism configured to couple staples to the living body tissue and adhesively connect a plurality of tissues using the staples in a state in which the plurality of tissues separated from each other are grasped by the pair of grasping parts.

4. The surgical instrument according to claim 1, wherein the first dissecting part has a first tissue separating structure set to a position at which a joinable region by the first joining part is interposed between the recessed portion and the first dissecting part and elongated in the longitudinal central axis direction, and the second dissecting part has a second tissue separating structure set to a position at which a joinable region by the first joining part is interposed between the recessed portion and the second dissecting part and elongated in the longitudinal central axis direction.

5. The surgical instrument according to claim 1, wherein a length of the first dissecting part measured along the longitudinal central axis direction is larger than that of the second dissecting part measured along the longitudinal central axis direction.

6. The surgical instrument according to claim 1, further comprising:
   an opening/closing operation part configured to open and close the pair of grasping parts;
   a joining operation part configured to join the living body tissue using at least one of the first joining part and the second joining part by individually moving the first joining part and the second joining part; and
   a separating operation part configured to cut the living body tissue using at least one of the first dissecting part and the second dissecting part by individually moving the first dissecting part and the second dissecting part according to operation that is different from operation of the joining operation part.

7. The surgical instrument according to claim 1, further comprising:
   an opening/closing operation part configured to open and close the pair of grasping parts; and
   a suture/separating simultaneous operation section configured to move the first joining part, the second joining part, the first dissecting part and the second dissecting part through a single operation.

* * * * *